United States Patent
Sasaki

(10) Patent No.: US 8,742,161 B2
(45) Date of Patent: Jun. 3, 2014

(54) PROCESS FOR PRODUCING OPTICALLY ACTIVE BICYCLO [3.1.0] HEXANE DERIVATIVE USING ENZYME

(75) Inventor: Joji Sasaki, Toshima-ku (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 58 days.

(21) Appl. No.: 13/510,375

(22) PCT Filed: Nov. 18, 2010

(86) PCT No.: PCT/JP2010/006756
§ 371 (c)(1),
(2), (4) Date: May 17, 2012

(87) PCT Pub. No.: WO2011/061934
PCT Pub. Date: May 26, 2011

(65) Prior Publication Data
US 2012/0232304 A1    Sep. 13, 2012

(30) Foreign Application Priority Data
Nov. 18, 2009    (JP) ................. 2009-262827

(51) Int. Cl.
*C07C 69/74* (2006.01)
*C12P 7/38* (2006.01)

(52) U.S. Cl.
USPC ......................................... 560/119; 435/135

(58) Field of Classification Search
None
See application file for complete search history.

(56) References Cited

U.S. PATENT DOCUMENTS

| | | | |
|---|---|---|---|
| 6,825,375 B2 | 11/2004 | Nakazato et al. | |
| 7,157,594 B2 | 1/2007 | Nakazato et al. | |
| 7,381,746 B2 | 6/2008 | Yasuhara et al. | |
| 7,960,579 B2 | 6/2011 | Yasuhara et al. | |
| 2011/0065934 A1 | 3/2011 | Hirotsuka et al. | |

FOREIGN PATENT DOCUMENTS

| | | | | |
|---|---|---|---|---|
| EP | 2298755 A1 | * | 3/2011 | ........... C07D 317/72 |
| WO | 02/00595 A1 | | 1/2002 | |
| WO | 03/061698 A1 | | 7/2003 | |
| WO | 2005/000790 A1 | | 1/2005 | |
| WO | 2005/000791 A1 | | 1/2005 | |
| WO | 20050047215 | | 5/2005 | |
| WO | 2009/142184 A1 | | 11/2009 | |

OTHER PUBLICATIONS

European Communication for EP 10831333.9 dated Mar. 14, 2013, with Supplementary European Search Report dated Mar. 1, 2013.
Theil et al., "Synthesis of (1 S,4R)-(-)-4-Hydroxy-2-cyclopentenyl Acetate by a Highly Enantioselective Enzyme-catalyzed Transesterification in Organic Solvents", Synthesis, Abstract No. XP-002693017, pp. 540-541 (Jul. 1988).
Shigetada Nakanishi, "Molecular Diversity of Glutamate Receptors and Implications for Brain Function", Science, 1992, pp. 597-603, vol. 258.
Darryle Schoepp et al., "Pharmacological and functional characteristics of metabotropic excitatory amino acid receptors", Trends in Pharmacological Sciences, 1990, pp. 508-515, vol. 11.
Darryle Schoepp et al., "Metabotropic glutamate receptors in brain function and pathology", Trends in Pharmacological Sciences, 1993, pp. 13-20, vol. 14, No. 1.
Atsuro Nakazato et al., "Synthesis in Vitro Pharmacology, Structure-Activity Relationships, and Pharmacokinetics of 3-Alkoxy-2-amino-6-fluorobicyclo[3.1.0]hexane-2,6-dicarboxylic Acid Derivatives as Potent and Selective Group II Metabotropic Glutamate Receptor Antagonists", Journal of Medicinal Chemistry, 2004, pp. 4570-4587, vol. 47.

(Continued)

*Primary Examiner* — Brandon Fetterolf
*Assistant Examiner* — Ana Z Muresan
(74) *Attorney, Agent, or Firm* — Sughrue Mion, PLLC

(57) ABSTRACT

There is provided a process for producing a bicyclo [3.1.0] hexane derivative represented by the formula (I) and a salt thereof including; causing an enzyme to act on an optically inactive compound represented by the formula (II) causing an asymmetric acylation reaction and a highly-stereoselective conversion to an optically active compound represented by the formula (III); and converting the compound represented by the formula (III) to the compound represented by the formula (I) or a salt thereof.

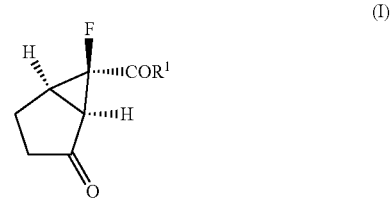

(I)

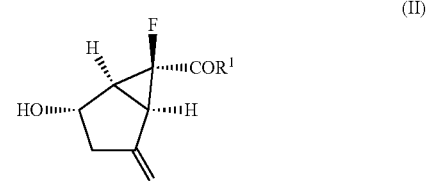

(II)

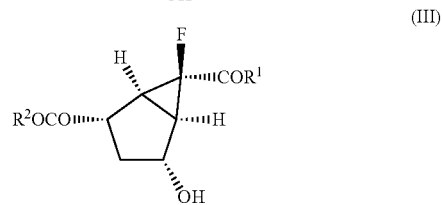

(III)

9 Claims, No Drawings

(56) References Cited

OTHER PUBLICATIONS

Akito Yasuhara et al., "Synthesis, in vitro pharmacology, and structure-activity relationships of 2-aminobicyclo[3.1.0]hexane-2,6-dicarboxylic acid derivatives as mGluR2 antagonists", Bioorganic & Medicinal Chemistry, 2006, pp. 3405-3420, vol. 14.

Akito Yasuhara et al., "Prodrugs of 3-(3,4-dichlorobenzyloxy)-2-amino-6-fluorobicyclo[3.1.0]hexane-2,6-dicarboxylic acid (MGS0039):A potent and orally active group II mGluR antagonist with antidepressant-like potential", Bioorganic & Medicinal Chemistry, 2006, pp. 4193-4207, vol. 14.

Fei Zhang et al., "Enantioselective Preparation of Ring-Fused 1-Fluorocyclopropane-1-carboxylate Derivatives: En Route to mGluR 2 Receptor Agonist MGS0028", Organic Letters, 2004, pp. 3775-3777, vol. 6, No. 21.

Atsuro Nakazato et al., "Synthesis, SARs, and Pharmacological Characterization of 2-Amino-3 or 6-fluorobicyclo[3.1.0]hexane-2,6-dicarboxylic Acid Derivatives as Potent, Selective, and Orally Active Group II Metabotropic Glutamate Receptor Agonists", Journal of Medicinal Chemistry, 2000, pp. 4893-4909, vol. 43.

Akio Saito et al., "A stereoselective preparation of 1-fluorocyclopropane-1-carboxylate derivatives through radical addition of fluoroiodoacetate to alkenes followed by intramolecular substitution reaction", Tetrahedron, 2001, pp. 7487-7493, vol. 57.

Audrey Wong et al., "Reactive resin facilitated preparation of an enantiopure fluorobicycloketone", Organic & Bimolecular Chemistry, 2004, pp. 168-174, vol. 2, No. 2.

International Search Report for PCT/JP2010/006756 dated Feb. 8, 2011.

* cited by examiner

PROCESS FOR PRODUCING OPTICALLY ACTIVE BICYCLO [3.1.0] HEXANE DERIVATIVE USING ENZYME

CROSS REFERENCE TO RELATED APPLICATIONS

This application is a National Stage of International Application No. PCT/JP2010/006756 filed Nov. 18, 2010, claiming priority based on Japanese Patent Application No. 2009-262827 filed Nov. 18, 2009, the contents of all of which are incorporated herein by reference in their entirety.

TECHNICAL FIELD

The present invention relates to a process for producing a bicyclo [3.1.0] hexane derivative, which is a metabotropic glutamate receptor modulator useful as a pharmaceutical. Furthermore, the invention relates to a novel intermediate compound produced in the above production process.

BACKGROUND ART

An excitatory amino acid such as glutamic acid modulates various physiological processes such as long term potentiation (learning and memory), synaptic plasticity development, motion control, respiration, cardiovascular modulation, and perception in the central nervous system (CNS) of a mammal.

Presently, glutamate receptors are classified into two major groups, that is, "an ionotropic type in which the receptor has an ion channel structure": ion channel type glutamate receptor (iGluR), and "a metabotropic type in which the receptor is coupled to a G protein": metabotropic glutamate receptor (mGluR) (see, Non-Patent Document 1). It appears that receptors of either class mediate normal synaptic transmission in accordance with an excitatory pathway. It also appears that they are involved in modification of synaptic binding from the development stage throughout the lifetime (see, Non-Patent Document 2).

Eight subtypes of the metabotropic glutamate receptor that have been identified so far are classified into three groups (group I, II, and III) depending on pharmacological characteristics and intracellular second messengers to which they are coupled. Of these, group II receptor (mGluR2/mGluR3) binds with adenylate cyclase, and inhibit the accumulation of cyclic adenosine-1-phosphate (cAMP) stimulated by forskolin (see, Non-Patent Document 3). Thus, it is suggested that compounds that antagonize the group II metabotropic glutamate receptors are effective for the treatment or prevention of acute and chronic psychiatric disorders and neurological diseases.

It is recognized that a 2-amino-6-fluoro bicyclo [3.1.0] hexane-2,6-dicarboxylic acid derivative having a substituent group on position 3 has a strong antagonistic effect on group II metabotropic glutamate receptors. As such, it is effective for the treatment and prevention of psychiatric disorders such as schizophrenia, anxiety, and related ailments thereof, bipolar disorder, or epilepsy, and also of neurological diseases such as drug dependence, cognitive disorders, Alzheimer's disease, Huntington's disease, Parkinson's disease, dyskinesia associated with muscular rigidity, cerebral ischemia, cerebral failure, encephalopathy, or head trauma (see, Patent Documents 1 to 3 and Non-Patent Documents 4 to 6).

For example, as an antagonist of group II metabotropic glutamate receptor, 2-amino-3-alkoxy-6-fluoro bicyclo [3.1.0] hexane-2,6-dicarboxylic acid derivative represented by the following formula (A), a pharmaceutically acceptable salt thereof, or a hydrate thereof is disclosed (see, Patent Document 1). Since those compounds are useful as a therapeutic agent, it is believed that development of a synthetic process suitable for commercial production thereof, that is effective in terms of cost and also can be carried out on a safe and large scale, is in need.

[Chemical Formula 1]

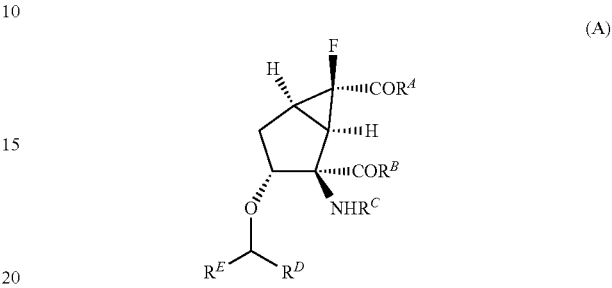

(A)

(in the formula (A), $R^A$ and $R^B$, which may be the same or different, each represents a hydroxyl group, a $C_{1-10}$ alkoxy group, a phenoxy group, a naphthyloxy group, a $C_{1-6}$ alkoxy group which is substituted with one or two phenyl groups, a $C_{1-6}$ alkoxy $C_{1-6}$ alkoxy group, a hydroxy $C_{2-6}$ alkoxy group, an amino group, an amino group which is substituted with the same or different one or two $C_{1-6}$ alkyl groups, an amino group which is substituted with the same or different one or two $C_{1-6}$ alkoxy $C_{1-6}$ alkyl groups, an amino group which is substituted with the same or different one or two hydroxy $C_{2-6}$ alkyl groups, an amino group which is substituted with the same or different one or two $C_{1-6}$ alkoxycarbonyl $C_{1-6}$ alkyl groups, or a native or non-native amino acid residue represented by $NR^F$—$CHR^G$—A—$CO_2R^H$ (in which $R^F$ and $R^G$, which may be the same or different, each represents a hydrogen atom, a hydroxy $C_{1-6}$ alkyl group, a hydroxycarbonyl $C_{1-6}$ alkyl group, a $C_{1-10}$ alkyl group, a phenyl group, a phenyl $C_{1-6}$ alkyl group, a hydroxyphenyl group, a hydroxyphenyl $C_{1-6}$ alkyl group, a naphthyl group, a naphthyl $C_{1-6}$ alkyl group, an aromatic heterocyclic $C_{1-6}$ alkyl group, a $C_{1-6}$ alkoxy $C_{1-6}$ alkyl group, an amino $C_{2-6}$ alkyl group, a guanidino $C_{2-6}$ alkyl group, a mercapto $C_{2-6}$ alkyl group, a $C_{1-6}$ alkylthio $C_{1-6}$ alkyl group, or an aminocarbonyl $C_{1-6}$ alkyl group, or $R^F$ and $R^G$ may bind to each other to represent a group capable of forming a methylene group, an ethylene group or a propylene group, or may together form a cyclic amino group; $R^H$ represents a hydrogen atom or a protecting group for carboxyl group; and A represents a single bond, a methylene group, an ethylene group or a propylene group); $R^C$ represents a $C_{1-10}$ acyl group, a $C_{1-6}$ alkoxy $C_{1-6}$ acyl group, a hydroxy $C_{2-10}$ acyl group, a $C_{1-6}$ alkoxycarbonyl $C_{1-6}$ acyl group, a hydroxycarbonyl $C_{1-6}$ acyl group, or an amino acid residue represented by $R^I$—NH—A—CH—$R^G$—CO (wherein $R^G$ and A are as defined above, and $R^I$ represents a hydrogen atom or a protecting group for amino group); and $R^D$ and $R^E$, which may be the same or different, each represents a hydrogen atom, a $C_{1-10}$ alkyl group, a $C_{2-10}$ alkenyl group, a phenyl group, a naphthyl group, a 5-membered heteroaromatic ring containing one or more heteroatoms, or a phenyl group substituted with 1 to 5 substituent groups selected from the group consisting of a halogen atom, a $C_{1-10}$ alkyl group, a $C_{1-10}$ alkoxy group, a trifluoromethyl group, a phenyl group, a hydroxycarbonyl group, an amino group, a nitro group, a cyano group, and a phenoxy group, or $R^D$ and $R^E$ may bind to each other to form a cyclic structure).

With respect to a lab-scale synthesis of antagonist substance of group II metabotropic glutamate receptor that is represented by the formula (A) and synthetic intermediate thereof, several studies have been made (see, Patent Documents 1 and 3 and Non-Patent Documents 4 and 6). For any process, an optically active compound represented by the following formula (IA) is used as a starting material for synthesis or as a production intermediate.

[Chemical Formula 2]

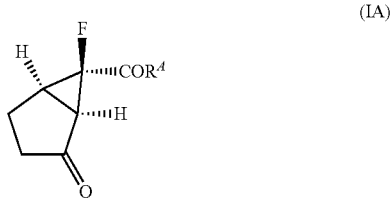

(IA)

($R^4$ in the above formula (IA) is as defined in the formula (A)).

Thus, from the viewpoint of establishing a process for industrial production of an antagonist substance of group II metabotropic glutamate receptor represented by the formula (A), which is believed to be useful as a therapeutic agent, it is important to develop a process of synthesizing an optically active compound represented by the formula (IA), that is effective in terms of cost, safety, and suitable for mass production. Non-Patent Document 7 discloses the enantiomer synthesis process of the optically active compound represented by the formula (IA). According to the synthetic process disclosed in Non-Patent Document 7, a catalytic asymmetric arylation developed by Trost, et al. is described as a process of synthesizing the optically active compound. By replacing the Trost ligand (N, N'-(1R, 2R)-cyclohexane-1,2-diylbis[2-diphenylphosphanylbenzamide]) that is used as an optically active ligand for the catalytic asymmetric arylation in Non-Patent Document 7 with its enantiomer (N, N'-(1S, 2S)-cyclohexane-1,2-diylbis[2-(diphenylphosphanyl)benzamide]), the optically active compound represented by the formula (IA) can be synthesized. Thus, it can be said that the asymmetric synthesis of the optically active compound represented by the formula (IA) is already disclosed in Non-Patent Document 7.

Further, a process of synthesizing a racemate of the compound represented by the formula (IA) is disclosed in Non-Patent Documents 8 and 9 and Patent Document 4. In Non-Patent Document 8, it is described that the optically active compound represented by the formula (IA) can be obtained by isolating racemate of the compound represented by the formula (IA) by using an HPLC column for isolating optical isomers. Further, in Non-Patent Document 10, it is disclosed that the optically active compound represented by the formula (IA) can be obtained with enantiomeric excess ratio of 38% and 54% based on a reaction which uses an asymmetric ligand. However, those synthetic processes essentially require an operation of isolating the optically active compound represented by the formula (IA) from enantiomers, and therefore it is difficult to say that they are more suitable for mass production than the asymmetric synthesis process disclosed in Non-Patent Document 7.

RELATED DOCUMENT

Patent Document

[Patent Document 1] International Publication No. 2003/061698

[Patent Document 2] International Publication No. 2005/000790

[Patent Document 3] International Publication No. 2005/000791

[Patent Document 4] International Publication No. 2002/000595

Non-Patent Document

[Non-Patent Document 1] Science, 258,597-603 (1992)

[Non-Patent Document 2] Trends Pharmacol. Sci., 11, 508-515 (1990)

[Non-Patent Document 3] Trends Pharmacol. Sci., 14, 13-20 (1993)

[Non-Patent Document 4] J. Med. Chem., 47, 4570-4587 (2004)

[Non-Patent Document 5] Bioorg. Med. Chem., 14, 3405-3420 (2006)

[Non-Patent Document 6] Bioorg. Med. Chem., 14, 4193-4207 (2006)

[Non-Patent Document 7] Org. Lett., 6, 3775-3777 (2004)

[Non-Patent Document 8] J. Med. Chem., 43, 4893-4909 (2000)

[Non-Patent Document 9] Tetrahedron, 57, 7487-7493 (2001)

[Non-Patent Document 10] Org. Biomol. Chem., 2, 168-174 (2004)

DISCLOSURE OF THE INVENTION

Problem to be Solved by the Invention

However, according to the conventional process for asymmetric synthesis of the compounds represented by the formula (IA) (Non-Patent Document 7), it is necessary to use an expensive chemical reagent like Trost ligand to obtain an optically active substance, and therefore production cost is extremely high. Based on such reasons and from the viewpoint of establishing an industrially suitable method for production of a compound represented by the formula (IA), a significant reduction in production cost has been remained as a problem to be solved.

Means for Solving Problem

As a result of an intensive investigation by the inventor of the present application, a novel production process, and a novel synthetic intermediate compound have been found for efficient synthesis of an optically active compound represented by the formula (I) with high optical purity from an optically inactive compound represented by the formula (II), which can be produced without using an expensive chemical reagent, by carrying out an asymmetric acylation by causing an enzyme to act on an optically inactive compound represented by the formula (II), developing a process of converting with high stereo selectivity the compound to an optically active compound represented by the following formula (III), and devising a novel synthetic pathway for converting the compound represented by the formula (III) to the compound represented by the following formula (I).

The invention is to provide a process for producing a bicyclo [3.1.0] hexane derivative represented by the formula (I) and a salt thereof which enables significant reduction in production cost compared to conventional processes, wherein the derivative is useful for production of an antagonist substance represented by the formula (A) that is a group II metabotropic glutamate receptor regarded as a useful therapeutic agent.

Specifically, the invention relates to (i) a process for producing a bicyclo [3.1.0] hexane derivative represented by the formula (I) and a salt thereof, including:

[Chemical Formula 3]

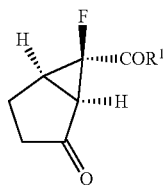

(I)

(in the formula (I), $R^1$ represents (1) —OH, (2) —O—$R^a$, or (3) —N$R^b R^c$, $R^a$ represents a $C_{1-6}$ alkyl group or a $C_{3-8}$ cycloalkyl group (wherein the $C_{1-6}$ alkyl group or the $C_{3-8}$ cycloalkyl group is either unsubstituted or substituted with one or more of a $C_{1-6}$ alkoxy group, a hydroxyl group, a halogen atom, an aryl group, or a heteroaryl group), $R^b$ and $R^b$, which may be the same or different from each other, each represents a hydrogen atom, a halogen atom, a $C_{1-6}$ alkyl group, or a $C_{3-8}$ cycloalkyl group (the $C_{1-6}$ alkyl group or the $C_{3-8}$ cycloalkyl group is either unsubstituted or substituted with one or more of a hydroxyl group, a $C_{1-6}$ alkoxy group, an aryl group, or a heteroaryl group), or $R^b$ and $R^c$ may bond to each other and form a 4- to 7-membered saturated heterocycle together with an adjacent nitrogen atom (wherein the saturated heterocycle is either unsubstituted or substituted with a hydroxyl group, a $C_{1-6}$ alkyl group, or a $C_{1-6}$ alkoxy group)), (A) converting a compound represented by the formula (II) to a compound represented by the formula (III),

[Chemical Formula 4]

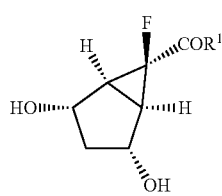

(II)

(in the formula (II), $R^1$ is as defined in the formula (I) above)

[Chemical Formula 5]

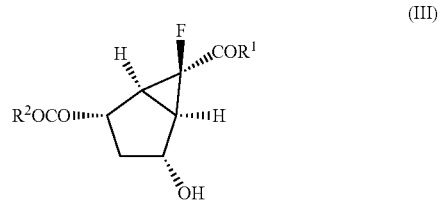

(III)

(in the formula (III), $R^1$ represents (1) —OH, (2) —O—$R^a$, or (3) —N$R^b R^c$, $R^a$ represents a $C_{1-6}$ alkyl group, or a $C_{3-8}$ cycloalkyl group (wherein the $C_{1-6}$ alkyl group or $C_{3-8}$ cycloalkyl group is either unsubstituted or substituted with one or more of a $C_{1-6}$ alkoxy group, a hydroxyl group, a halogen atom, an aryl group, or a heteroaryl group), $R^b$ and $R^b$, which may be the same or different from each other, each represents a hydrogen atom, a halogen atom, a $C_{1-6}$ alkyl group, or a $C_{3-8}$ cycloalkyl group (wherein the $C_{1-6}$ alkyl group or $C_{3-8}$ cycloalkyl group is either unsubstituted or substituted with one or more of a hydroxyl group, a $C_{1-6}$ alkoxy group, an aryl group, or a heteroaryl group), or $R^b$ and $R^b$ form a 4- to 7-membered saturated heterocycle together with an adjacent nitrogen atom (wherein the saturated heterocycle is either unsubstituted or substituted with a hydroxyl group, a $C_{1-6}$ alkyl group, or a $C_{1-6}$ alkoxy group), $R^2$ represents a hydrogen atom, a $C_{1-6}$ alkyl group, a $C_{3-8}$ cycloalkyl group, or a —$(CH_2)_n$-phenyl group (wherein the $C_{1-6}$ alkyl group, $C_{3-8}$ cycloalkyl group, or —$(CH_2)_n$-phenyl group is either unsubstituted or substituted with one or more of a halogen atom, a hydroxyl group, a $C_{1-6}$ alkyl group, or a $C_{1-6}$ alkoxy group), and n represents 0, 1, or 2), (B) converting the compound represented by the formula (III) to a compound represented by the formula (IV),

[Chemical Formula 6]

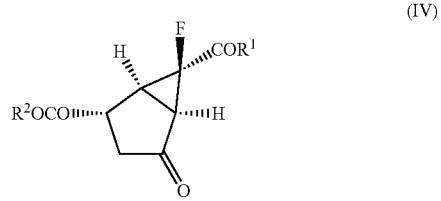

(IV)

(in the formula (IV), $R^1$ and $R^2$ are as defined in the formula (I) and the formula (III) above), (C) converting the compound represented by the formula (IV) to a compound represented by the formula (V),

[Chemical Formula 7]

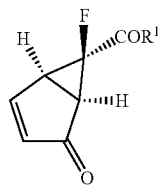

(V)

(in the formula (V), $R^1$ is as defined in the formula (I) above), and (D) converting the compound represented by the formula (V) to the compound represented by the formula (I), (ii) A process for producing a compound represented by the formula (III) or a salt thereof, which includes converting a compound represented by the formula (II) to the compound represented by the formula (III),

[Chemical Formula 8]

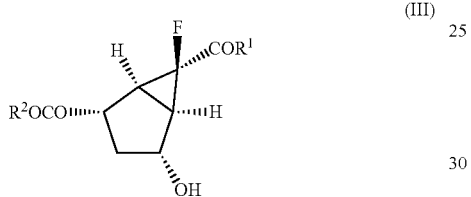

(III)

(in the formula (III), $R^1$ is as defined in the formula (I) above, $R^2$ represents a hydrogen atom, a $C_{1-6}$ alkyl group, a $C_{3-8}$ cycloalkyl group, or a —$(CH_2)_n$-phenyl group (wherein the $C_{1-6}$ alkyl group, $C_{3-8}$ cycloalkyl group, or —$(CH_2)_n$-phenyl group is either unsubstituted or substituted with one or more of a halogen atom, a hydroxyl group, a $C_{1-6}$ alkyl group, or a $C_{1-6}$ alkoxy group), and n represents 0, 1, or 2)

[Chemical Formula 9]

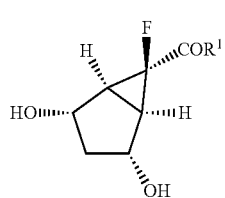

(II)

(in the formula (II), $R^1$ is as defined in the formula (III) above), (iii) The process described in above (i) or (ii), wherein $R^1$ is (2)—O—$R^a$ and $R^a$ is a methyl group or an ethyl group, (iv) The process described in any one of above (i) to (iii), wherein $R^2$ is a methyl group, (v) The process described in any one of above (i) to (iv), wherein the step of converting the compound represented by the formula (II) to the compound represented by the formula (III) includes reacting the compound represented by the formula (II) with an acyl group donor in the presence of an enzyme derived from a microorganism to produce the compound represented by the formula (III), (vi) The process described in above (v), wherein the microorganism is at least one selected from the group consisting of the genus *Candida*, the genus *Aspergillus*, the genus *Thermomyces*, the genus *Penicillium*, the genus *Alcaligenes*, the genus *Geotrichum*, the genus *Galactomyces*, and the genus *Dipodascus*, (vii) The process described in above (v) or (vi), wherein the enzyme derived from a microorganism is a lipase, a protease, or a pectinase, (viii) The process described in above (v), wherein the enzyme derived from a microorganism is a lipase derived from *Candida cylindracea*, *Candida rugosa*, or *Alcaligenes* sp, (ix) The process described in any one of above (v) to (viii), wherein the enzyme is immobilized on a support, (x) The process described in any one of above (v) to (ix), wherein the acyl group donor is vinyl acetate or isopropenyl acetate, (xi) A compound represented by the formula (III) or a salt thereof

[Chemical Formula 10]

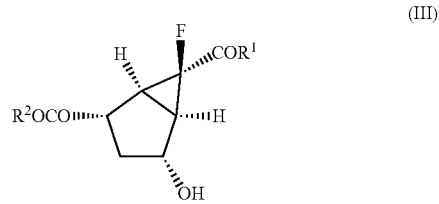

(III)

(in the formula (III), $R^1$ represents (1) —OH, (2) —O—$R^a$, or (3) —$NR^bR^c$, $R^a$ represents a $C_{1-6}$ alkyl group or a $C_{3-8}$ cycloalkyl group (wherein the $C_{1-6}$ alkyl group or $C_{3-8}$ cycloalkyl group is either unsubstituted or substituted with one or more of a $C_{1-6}$ alkoxy group, a hydroxyl group, a halogen atom, an aryl group, or a heteroaryl group), $R^b$ and $R^c$, which may be the same or different from each other, each represents a hydrogen atom, a halogen atom, a $C_{1-6}$ alkyl group, or a $C_{3-8}$ cycloalkyl group (wherein the $C_{1-6}$ alkyl group or $C_{3-8}$ cycloalkyl group is either unsubstituted or substituted with one or more of a hydroxyl group, a $C_{1-6}$ alkoxy group, an aryl group, or a heteroaryl group), or $R^b$ and $R^c$ bond to each other and form a 4- to 7-membered saturated heterocycle together with an adjacent nitrogen atom (wherein the saturated heterocycle is either unsubstituted or substituted with a hydroxyl group, a $C_{1-6}$ alkyl group, or a $C_{1-6}$ alkoxy group), $R^2$ represents a hydrogen atom, a $C_{1-6}$ alkyl group, a $C_{3-8}$ cycloalkyl group, or a —$(CH_2)_n$-phenyl group (wherein the $C_{1-6}$ alkyl group, $C_{3-8}$ cycloalkyl group, or —$(CH_2)_n$-phenyl group is either unsubstituted or substituted with one or more of a halogen atom, a hydroxyl group, a $C_{1-6}$ alkyl group, or a $C_{1-6}$ alkoxy group), and n represents 0, 1, or 2), or (xii) A compound represented by the formula (IV) or a salt thereof

[Chemical Formula 11]

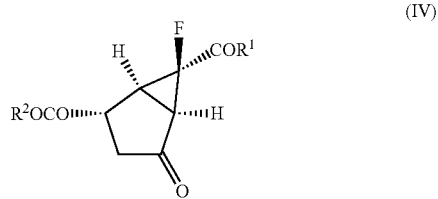

(in the formula (IV), $R^1$ represents
(1) —OH,
(2) —O—$R^a$, or
(3) —$NR^bR^c$,
$R^a$ represents a $C_{1-6}$ alkyl group or a $C_{3-8}$ cycloalkyl group (wherein the $C_{1-6}$ alkyl group or $C_{3-8}$ cycloalkyl group is either unsubstituted or substituted with one or more of a $C_{1-6}$ alkoxy group, a hydroxyl group, a halogen atom, an aryl group, or a heteroaryl group),
$R^b$ and $R^c$, which may be the same or different from each other, each represents a hydrogen atom, a halogen atom, a $C_{1-6}$ alkyl group, or a $C_{3-8}$ cycloalkyl group (wherein the $C_{1-6}$ alkyl group or $C_{3-8}$ cycloalkyl group is either unsubstituted or substituted with one or more of a hydroxyl group, a $C_{1-6}$ alkoxy group, an aryl group, or a heteroaryl group), or $R^b$ and $R^c$ bond to each other and form a 4- to 7-membered saturated heterocycle together with an adjacent nitrogen atom (wherein the saturated heterocycle is either unsubstituted or substituted with a hydroxyl group, a $C_{1-6}$ alkyl group, or a $C_{1-6}$ alkoxy group), $R^2$ represents a hydrogen atom, a $C_{1-6}$ alkyl group, a $C_{3-8}$ cycloalkyl group, or a —$(CH_2)_n$-phenyl group (wherein the $C_{1-6}$ alkyl group, $C_{3-8}$ cycloalkyl group, or —$(CH_2)_n$-phenyl group is either unsubstituted or substituted with one or more of a halogen atom, a hydroxyl group, a $C_{1-6}$ alkyl group, or a $C_{1-6}$ alkoxy group), and n represents 0, 1, or 2).

Advantageous Effects of Invention

According to the invention, use of an expensive chemical reagent like Trost ligand, which has been considered to be essential for production of the bicyclo [3.1.0] hexane derivative represented by the formula (I) and a salt thereof, that is useful as a therapeutic agent, and useful for production of an antagonist substance of group II metabotropic glutamate receptor represented by the formula (A), can be avoided, and therefore a significant reduction in production cost can be achieved.

DESCRIPTION OF EMBODIMENTS

In the specification, the numerical range described with "-" or "to" includes the value of both ends, unless specifically described otherwise.

The "$C_{1-6}$ alkyl group" denotes a straight chain or branched alkyl group having 1 to 6 carbon atoms, and examples thereof include methyl, ethyl, n-propyl, isopropyl, n-butyl, isobutyl, sec-butyl, tert-butyl, n-pentyl, isopentyl, neopentyl, and n-hexyl groups.

The "$C_{3-8}$ cycloalkyl group" denotes a cyclic alkyl group having 3 to 8 carbon atoms, and examples thereof include cyclopropyl, cyclobutyl, cyclopentyl, cyclohexyl, cycloheptyl, and cyclooctyl groups.

The "$C_{1-6}$ alkoxy group" denotes a straight chain or branched alkoxy group having 1 to 6 carbon atoms, and examples thereof include methoxy, ethoxy, n-propoxy, isopropoxy, n-butoxy, isobutoxy, sec-butoxy, tert-butoxy, n-pentyloxy, isopentyloxy, neopentyloxy, and n-hexyloxy groups.

The "halogen atom" is a fluorine atom, a chlorine atom, a bromine atom, or an iodine atom.

The "aryl group" denotes an aromatic hydrocarbon substituent group and may be monocyclic or polycyclic (preferably monocyclic to tricyclic), and the rings in the polycycle may or may not be fused. Examples thereof include phenyl, naphthyl, and biphenyl groups.

The "heteroaryl group" denotes an aromatic ring having at least one heteroatom (nitrogen, oxygen, or sulfur) in the ring skeleton. The heteroaryl group may be monocyclic or polycyclic (preferably monocyclic to tricyclic), and the rings in the polycycle may or may not be fused. Examples thereof include groups such as pyrrole, pyrazole, imidazole, pyridine, pyrazine, pyrimidine, furan, pyran, oxazole, isooxazole, purine, benzimidazole, quinoline, isoquinoline, and indole. When the heteroaryl group defined here is substituted, the substituent group may be bonded to a carbon atom forming the ring of the heteroaryl group or may be bonded to a nitrogen atom forming the ring, and has a valence that enables substitution. The substituent group is preferably bonded to a carbon atom forming the ring.

The term "bonding to each other and, together with the adjacent nitrogen atom, forming a 4- to 7-membered saturated heterocycle" denotes groups such as azetidinyl, pyrrolidinyl, piperidinyl, or azepanyl.

The term "enzyme derived from a microorganism" denotes for example an enzyme derived from a microorganism such as a fungus or a bacterium, and may be obtained from an extract in which such a microorganism is disrupted or a culture supernatant of such a microorganism. As the enzyme, there can be cited a lipase, an acylase, a protease, a pectinase, and the like; it is not limited to one type, and a plurality of enzymes may be present simultaneously. Examples of the fungus include the genus *Candida*, the genus *Aspergillus*, the genus *Thermomyces*, the genus *Penicillium*, the genus *Geotrichum*, the genus *Galactomyces*, and the genus *Dipodascus*. Examples of the bacterium include the genus *Alcaligenes*.

The term "support" is not particularly limited as long as it is a support that can immobilize an enzyme; examples thereof include Celite (trade name), which is a diatomaceous earth calcined together with sodium carbonate, and Toyonite (trade name), which is a porous ceramic-based support obtained by hydrothermally processing a kaolin mineral under hydrochloric acid-acidified conditions, then granulating, and calcining it. It is possible to easily modify the surface of Toyonite particles with various organic functional groups. By changing the type of organic functional group (methacryloyloxy group, phenylamino group, amino group, and the like) of a coupling agent used for modification of the surface of Toyonite, various types of enzyme may be more selectively immobilized. By immobilizing an enzyme on a simple substance such as Celite or Toyonite, the stability, reaction activity, and the like of the enzyme are increased.

The term "salt" includes, for example, a salt with an inorganic acid such as sulfuric acid, hydrochloric acid, hydrobromic acid, phosphoric acid, or nitric acid; a salt with an organic acid such as acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid, or naphthalene-2-sulfonic acid;

a salt with one or more types of metal ions such as lithium ion, sodium ion, potassium ion, calcium ion, magnesium ion, zinc ion, or aluminum ion; or a salt with an amine such as ammonia, arginine, lysine, piperazine, choline, diethylamine, 4-phenylcyclohexylamine, 2-aminoethanol, or benzathine.

The term "enantiomerically pure" denotes that a target enantiomer is present in at least 50% e.e. (enantiomeric excess) or more relative to an untargeted enantiomer, preferably at least 80% e.e. or more, and yet more preferably at least 90% e.e. or more.

A preferred embodiment of the process for producing the compound represented by the formula (I) in the invention employs the compound represented by the formula (II) as a starting material. It is preferable that $R^1$ is (1) —OH, (2) —O—$R^a$, $R^a$ is a $C_{1-6}$ alkyl group, or (3) —N$R^b R^c$, and both $R^b$ and $R^c$ are a hydrogen atom. More preferably, $R^1$ is (2) —O—$R^a$ and $R^a$ is a methyl group or an ethyl group. Particularly preferably, $R^1$ is (2) —O—$R^a$ and $R^a$ is a methyl group.

A preferred embodiment of the process for producing the compound represented by the formula (V) in the invention employs the compound represented by the formula (II) as a starting material. It is preferable that $R^1$ is (1) —OH, (2) —O—$R^a$, $R^a$ is a $C_{1-6}$ alkyl group, or (3) —N$R^b R^c$, and both $R^b$ and $R^c$ are a hydrogen atom. More preferably, $R^{1}$ is (2) —O—$R^a$ and $R^a$ is a methyl group or an ethyl group. Particularly preferably, $R^1$ is (2) —O—$R^a$ and $R^a$ is a methyl group.

A preferred embodiment of the process for producing the compound represented by the formula (IV) in the invention employs the compound represented by the formula (II) as a starting material. It is preferable that $R^1$ is (1) —OH, (2) —O—$R^a$, $R^a$ is a $C_{1-6}$ alkyl group, or (3) —N$R^b R^c$, and both $R^b$ and $R^c$ are a hydrogen atom, and $R^2$ is a $C_{1-6}$ alkyl group, a $C_{3-8}$ cycloalkyl group, or a —(CH$_2$)$_n$-phenyl group. More preferably, $R^1$ is (2) —O—$R^a$, $R^a$ is a methyl group or an ethyl group, and $R^2$ is a methyl group, an ethyl group, a propyl group, a butyl group, a heptyl group, a monochloromethyl group, or a phenyl group. Particularly preferably, $R^1$ is (2) —O—$R^a$, $R^a$ is a methyl group, and $R^2$ is a methyl group.

A preferred embodiment of the process for producing the compound represented by the formula (III) in the invention employs the compound represented by the formula (II) as a starting material. It is preferable that $R^1$ is (1) —OH, (2) —O—$R^a$, $R^a$ is a $C_{1-6}$ alkyl group, or (3) —N$R^b R^c$, and both $R^b$ and $R^c$ are a hydrogen atom, and $R^2$ is a $C_{1-6}$ alkyl group, a $C_{3-8}$ cycloalkyl group, or a —(CH$_2$)$_n$-phenyl group. More preferably, $R^1$ is (2) —O—$R^a$, $R^a$ is a methyl group or an ethyl group, and $R^2$ is a methyl group, an ethyl group, a propyl group, a butyl group, a heptyl group, a monochloromethyl group, or a phenyl group. Particularly preferably, $R^1$ is (2) —O—$R^a$, $R^a$ is a methyl group, and $R^2$ is a methyl group.

One embodiment of the production process of the invention is shown in the Scheme 1 and the Scheme 2 below.

SCHEME 1

(Scheme 1)

[Chemical Formula 12]

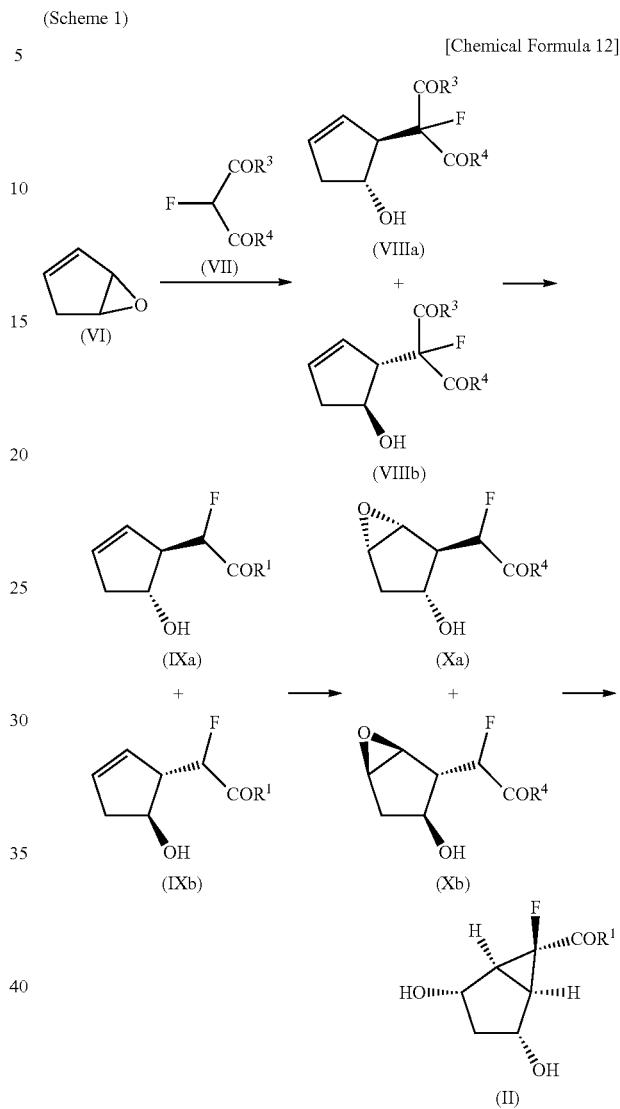

In the formulae of the Scheme 1, $R^1$ is as defined above. $R^3$ and $R^4$ represent (1) —OH, (2) —O—$R^a$, or (3) —N$R^b R^c$, $R^a$ represents a $C_{1-6}$ alkyl group or a $C_{3-8}$ cycloalkyl group (wherein the $C_{1-6}$ alkyl group or the $C_{3-8}$ cycloalkyl group is either unsubstituted or substituted with one or more of a $C_{1-6}$ alkoxy group, a hydroxyl group, a halogen atom, an aryl group, or a heteroaryl group), $R^b$ and $R^c$, which may be the same or different from each other, each represents a hydrogen atom, a halogen atom, a $C_{1-6}$ alkyl group, or a $C_{3-8}$ cycloalkyl group (the $C_{1-6}$ alkyl group or the $C_{3-8}$ cycloalkyl group is either unsubstituted or substituted with one or more of a hydroxyl group, a $C_{1-6}$ alkoxy group, an aryl group, or a heteroaryl group), or $R^b$ and $R^c$ may form a 4- to 7-membered saturated heterocycle together with an adjacent nitrogen atom (wherein the saturated heterocycle is either unsubstituted or substituted with a hydroxyl group, a $C_{1-6}$ alkyl group, or a $C_{1-6}$ alkoxy group).

The compound represented by the formula (VI) may be an optically active substance or an optically inactive substance. The compound represented by the formula (VI) may be synthesized by oxidizing cyclopentadiene using, for example, a peracid such as peracetic acid (J. Am. Chem. Soc., 82, 4328 (1960), Org. Synth., 42, 50 (1962)., Org. Lett., 7, 4573 (2005)). Furthermore, an optically active substance of the compound represented by the formula (VI) may be synthesized by asymmetric oxidation of cyclopentadiene in the presence of, for example, a metal catalyst (Synlett, 827 (1995), Tetrahedron Letters, 37, 7131 (1996), Japanese Patent Application Laid-Open No. H09-052887).

By reacting the compound represented by the formula (VI) and the compound represented by the formula (VII) in the presence of a base, a mixture of the compound represented by the formula (VIIIa) and the compound represented by the formula (VIIIb) is obtained.

Herein, it is preferable that $R^3$ and $R^4$, which may be the same or different from each other, represent a hydroxyl group, a $C_{1-6}$ alkoxy group, or an amino group. More preferably, $R^3$ and $R^4$ are a methoxy group or an ethoxy group. Particularly preferably, they are a methoxy group.

Examples of the base used in the reaction include an alkali metal alkoxide such as sodium methoxide, sodium ethoxide, or potassium tert-butoxide; an alkali metal hydride such as sodium hydride or potassium hydride; an alkali metal hydroxide such as sodium hydroxide or potassium hydroxide; an organic amine such as 1,8-diazabicyclo [5.4.0]-7-undecene, and; a metal amide such as lithium diisopropylamide or lithium hexamethyldisilazide; it is preferable to use an alkali metal alkoxide, it is more preferable to use an alkali metal methoxide or an alkali metal ethoxide, and it is yet more preferable to use sodium methoxide.

The amount of base used is not particularly limited as long as it is an amount that does not inhibit the reaction and does not cause a side reaction, but it may usually be used in the range of 0.5 to 5 molar equivalents relative to the compound represented by the formula (VI), preferably in the range of 1 to 3 molar equivalents, and more preferably in the range of 1 to 2 molar equivalents.

The amount of compound represented by the formula (VII) used is not particularly limited as long as it is an amount that does not inhibit the reaction and does not cause a side reaction, but it may usually be used in the range of 0.5 to 5 molar equivalents relative to the compound represented by the formula (VI), preferably in the range of 1 to 3 molar equivalents, and more preferably in the range of 1 to 2.5 molar equivalents.

A solvent used in the reaction is not particularly limited as long as it is stable under relevant reaction conditions and does not inhibit a target reaction, but since the yield of the mixture of the compound represented by the formula (VIIIa) and the compound represented by the formula (VIIIb), which are products, depends on the type of solvent, it is preferable to use an alcohol, and more preferably methanol, as a solvent.

The amount of reaction solvent used is usually 1 to 100 times by mass relative to the compound represented by the formula (VI), and preferably in the range of 5 to 30 times by mass.

The reaction temperature may be usually equal to or more than −80° C. and equal to or less than the boiling point of the solvent used, is preferably in the range of −20 to 60° C., and is more preferably in the range of 20 to 40° C.

Subsequently, by heating the mixture of the compound represented by the formula (VIIIa) and the compound represented by the formula (VIIIb) in the presence of an additive, a mixture of the compound represented by the formula (IXa) and the compound represented by the formula (IXb) is obtained.

A solvent used in the reaction is not particularly limited as long as it is stable under relevant reaction conditions and does not inhibit the target reaction. Since the yield of the mixture of the compound represented by the formula (IXa) and the compound represented by the formula (IXb), which are products, depends on the type of solvent, it is preferable to use a mixture of water and a polar organic solvent, more preferably water and dimethyl sulfoxide, and yet more preferably water and dimethyl sulfoxide at a ratio in the range of 0:5 to 1:5.

The amount of reaction solvent used may be usually 1 to 100 times by mass relative to the mixture of the compound represented by the formula (VIIIa) and the compound represented by the formula (VIIIb), is preferably in the range of 1 to 20 times by mass, and is more preferably in the range of 1 to 10 times by mass.

The reaction temperature may usually be 80° C. to 200° C., but is preferably in the range of 90° C. to 160° C., and more preferably in the range of 100 to 130° C.

When the reaction temperature exceeds the boiling point of the solvent used, the reaction may be carried out in a pressure-resistant vessel such as an autoclave.

Furthermore, the present reaction is accelerated by addition of the additive; examples of the additive that can be used include a salt, preferably an alkali metal halide salt such as lithium chloride, sodium chloride, potassium chloride, lithium bromide, sodium bromide, potassium bromide, lithium iodide, sodium iodide, or potassium iodide; an alkali metal cyanide salt such as sodium cyanide; a quaternary ammonium salt such as tetra-n-butyl ammonium chloride, tetra-n-butyl ammonium bromide, or tetra-n-butyl ammonium iodide; or an organic amine salt such as triethylamine hydrochloride salt, or a mixture thereof. It is also possible to use an alkali metal halide salt such as sodium chloride and an acid such as acetic acid in combination.

The amount of additive used is not particularly limited as long as it is an amount that does not inhibit the reaction and does not cause a side reaction, but it is usually in the range of 0.5 to 5 molar equivalents relative to the mixture of the compound represented by the formula (VIIIa) and the compound represented by the formula (VIIIb), preferably in the range of 1 to 4 molar equivalents, and more preferably in the range of 1 to 3 molar equivalents.

Subsequently, the mixture of the compound represented by the formula (IXa) and the compound represented by the formula (IXb) is oxidized in the presence of an additive, thus giving a mixture of the compound represented by the formula (Xa) and the compound represented by the formula (Xb).

The present reaction proceeds by adding an oxidizing agent such as tert-butyl hydroperoxide in the presence of a catalyst such as vanadyl acetylacetonate ($VO(acac)_2$).

A solvent used in the reaction is not particularly limited as long as it is stable under relevant reaction conditions and does not inhibit the target reaction. Since the yield of the mixture of the compound represented by the formula (Xa) and the compound represented by the formula (Xb), which are products, depends on the type of solvent, it is preferable to use an aromatic hydrocarbon or a halogenated hydrocarbon, more preferably chlorobenzene or toluene, and yet more preferably chlorobenzene.

The amount of reaction solvent used may be 3 to 100 times by mass relative to the mixture of the compound represented by the formula (IXa) and the compound represented by the formula (IXb), is preferably 3 to 20 times by mass, and is more preferably 5 to 10 times by mass.

The reaction temperature may usually be 0° C. to 100° C., but is preferably in the range of 30° C. to 80° C., and more preferably 50 to 60° C.

The amount of oxidizing agent used is not particularly limited as long as it is an amount that does not inhibit the reaction and does not cause a side reaction, but it may usually be used at 1 to 3 molar equivalents relative to the mixture of the compound represented by the formula (IXa) and the compound represented by the formula (IXb), and is preferably in the range of 1 to 2 molar equivalents.

The amount of catalyst used is not particularly limited as long as it is an amount that does not inhibit the reaction and does not cause a side reaction, but it may usually be used at 0.01 to 1 molar equivalents relative to the mixture of the compound represented by the formula (IXa) and the compound represented by the formula (IXb), and is preferably in the range of 0.2 to 0.5 molar equivalents.

Furthermore, epoxidation of the mixture of the compound represented by the formula (IXa) and the compound represented by the formula (IXb) may also be carried out by reacting with a halogenating agent such as N-bromosuccinimide or N-iodosuccinimide in an appropriate solvent (for example, a mixture of dimethyl sulfoxide and water) to convert them into halohydrin derivatives, and then treating with a base such as 1,8-diazabicyclo [5.4.0]-7-undecene.

Subsequently, by subjecting the mixture of the compound represented by the formula (Xa) and the compound represented by the formula (Xb) to an intramolecular cyclopropanation accompanied by epoxide ring opening, the compound represented by the formula (II) is obtained.

This reaction proceeds by adding a base in the presence of a Lewis acid.

In a preferred embodiment, first, the mixture of the compound represented by the formula (Xa) and the compound represented by the formula (Xb) is treated with a Lewis acid, and a base is then added. The compound represented by the formula (II) is obtained as the desired stereoisomer.

Examples of the Lewis acid include $R_3Al$, $R_2AlX$, $RAlX_2$, $Al(OR)_3$, $Ti(OR)_4$, $RTi(OR)_3$, $R_2Ti(OR)_2$, a $BF_3$ ether complex, $Et_2Zn$, and $Sc(OTf)_3$; it is preferably $Et_3Al$, $Al(OiPr)_3$, $Ti(OiPr)_4$, a $BF_3$ ether complex, $Et_2Zn$, and $Sc(OTf)_3$, more preferably $Et_3Al$, $Et_2AlCl$, and $Et_2Zn$, and yet more preferably $Et_3Al$. Here, X is a halogen atom or an inorganic radical, and each of the Rs is hydrocarbon group.

Further, in the present specification, "Et" is an abbreviation of ethyl, "Tf" is an abbreviation of trifluoromethane sulfonic acid, and "iPr" is an abbreviation of isopropyl.

The amount of Lewis acid used is not particularly limited as long as it is an amount that does not inhibit the reaction and does not cause a side reaction, but it may usually be used in the range of 1 to 5 molar equivalents relative to the mixture of the compound represented by the formula (Xa) and the compound represented by the formula (Xb), preferably in the range of 1.5 to 3 molar equivalents, and more preferably in the range of 2 to 2.5 molar equivalents.

Examples of the base include lithium hexamethyldisilazide and lithium diisopropylamide, and it is preferably lithium hexamethyldisilazide.

The amount of base used is not particularly limited as long as it is an amount that does not inhibit the reaction and does not cause a side reaction, but it may usually be used in the range of 1 to 5 molar equivalents relative to the mixture of the compound represented by the formula (Xa) and the compound represented by the formula (Xb), preferably in the range of 1.5 to 3 molar equivalents, and more preferably in the range of 2 to 2.5 molar equivalents.

A solvent used in the reaction is not particularly limited as long as it is stable under relevant reaction conditions and does not inhibit the target reaction. Since the yield of the compound represented by the formula (II), which is a product, depends on the type of solvent, it is preferable to use an ether-based solvent such as tetrahydrofuran (THF).

With regard to the amount of reaction solvent used, it may be used at 1 to 100 times by mass relative to the mixture of the compounds represented by the formula (Xa) and the compound represented by the formula (Xb), is preferably in the range of 3 to 20 times by mass, and is more preferably in the range of 5 to 10 times by mass.

The reaction temperature may usually be −80° C. to 0° C., and is preferably −60° C. to −40° C.

The reaction time is usually 0.5 hours to 6 hours, and is preferably 1 to 3 hours.

Furthermore, the hydroxyl group of the mixture of the compound represented by the formula (Xa) and the compound represented by the formula (Xb) may be protected by a tert-butyl dimethylsilyl group and the like and then subjected to a cyclopropanation reaction. By building a cyclopropane ring and then removing the protecting group, the compound represented by the formula (II) is obtained.

SCHEME 2

(Scheme 2)

[Chemical Formula 13]

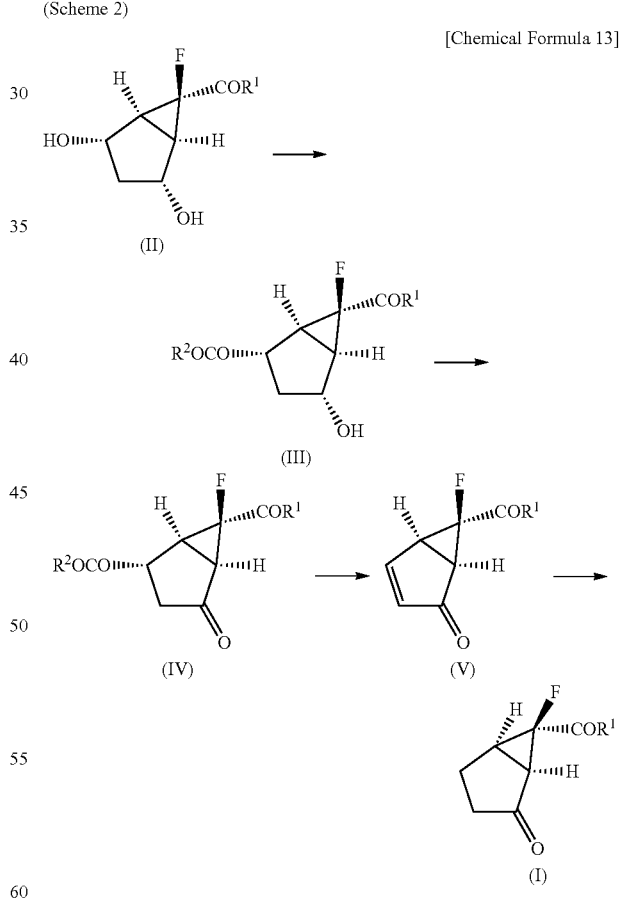

In the formulae of the Scheme 2, $R^1$ and $R^2$ are as defined above.

By stereoselectively protecting only one of the two hydroxyl groups of the compound represented by the formula (II), the compound represented by the formula (III) is obtained.

The present reaction gives a desired stereoisomer in the presence of an appropriate enzyme.

In a preferred embodiment of the present reaction, by reacting the compound represented by the formula (II) with an acyl group donor in the presence of an enzyme, the compound represented by the formula (III) is obtained.

As the enzyme, a microorganism-produced enzyme having stereoselective acylation capability is used. By reacting the compound represented by the formula (II) and an acyl group donor in an organic solvent and the like in the presence of this enzyme, stereoselective acylation can be carried out. Furthermore, by immobilizing the enzyme on a support, it may also be used in the reaction as an immobilized enzyme. In this case, after the compound represented by the formula (II) is mixed with an acyl group donor in an organic solvent and the like, the support having an enzyme immobilized thereon is added to the above mixture and stirred, or a column is charged with the support having an enzyme immobilized thereon, and the above mixture is passed through the column, thus carrying out a stereoselective acylation reaction. The reaction temperature may usually be −20° C. to 60° C. The organic solvent and the like used are not particularly limited as long as it is stable under relevant reaction conditions and does not inhibit the target reaction. Since the yield and optical purity of the compound represented by the formula (III), which is a product, depend on the type of solvent, it is preferable to use an organic solvent such as toluene, isopropyl ether, tetrahydrofuran, n-hexane, n-heptane, acetone, or chloroform or an ionic fluid such as 1-butyl-3-methylimidazolium hexafluorophosphate or 1-butyl-3-methylimidazolium tetrafluoroborate (Org. Lett., 2, 4189 (2000)).

Examples of the acyl group donor include vinyl acetate, isopropenyl acetate, vinyl propionate, isopropenyl propionate, vinyl butyrate, isopropenyl butyrate, vinyl caproate, isopropenyl caproate, vinyl caprate, isopropenyl caprate, vinyl caprylate, isopropenyl caprylate, vinyl chloroacetate, isopropenyl chloroacetate, vinyl pivalate, and isopropenyl pivalate, and it is preferably vinyl acetate or isopropenyl acetate. More preferably, it is vinyl acetate.

The microorganism as an enzyme source is preferably a fungus or a bacterium. It is more preferably at least one type of fungus or bacterium selected from the group consisting of the genus *Candida*, the genus *Aspergillus*, the genus *Thermomyces*, the genus *Penicillium*, the genus *Geotrichum*, the genus *Galactomyces*, the genus *Dipodascus*, and the genus *Alcaligenes*, and it is yet more preferably at least one type of fungus or bacterium selected from the group consisting of *Candida cylindracea, Candida rugosa, Aspergillus pulverulentus, Aspergillus niger, Aspergillus oryzae, Thermomyces langinosus, Penicillium roqueforti, Penicillium citrinum, Geotrichum fermentans, Galactomyces aurantii, Galactomyces reessii, Dipodascus australiensis*, and *Alcaligenes* sp.

The microorganism-derived enzyme is preferably a lipase, a protease, or a pectinase, and particularly preferably a lipase derived from *Candida cylindracea, Candida rugosa, Penicillium roqueforti*, or *Alcaligenes* sp. Most preferably, it is a lipase derived from *Candida cylindracea, Candida rugosa*, or *Alcaligenes* sp. The microorganism-derived enzyme may be purified from an extract in which a microorganism is disrupted or a culture supernatant in accordance with a standard method. It is not always necessary to purify the microorganism-derived enzyme as a single product, and it may also be used as a crude enzyme. The enzyme may be used either singly or a mixture of types thereof may be used as a mixture. It is also possible to obtain a commercial product.

Examples of commercially available products of *Candida cylindracea*-derived lipase include Lipase OF (trade name, available from Meito Sangyo. Co.) and also Lipase from *Candida cylindracea* (trade name, available from Sigma-Aldrich Japan Co.).

Examples of commercially available products of Candida rugosa-derived lipase include Lipase AY "Amano" 30G (trade name, available from, Amano enzyme), Lipase AYS "Amano" (trade name, available from Amano enzyme), and Lipase from *Candida rugosa* (trade name, available from Sigma-Aldrich Japan Co.).

Examples of commercially available products of *Penicillium roqueforti*-derived lipase include Lipase R (trade name, available from Amano enzyme).

Examples of commercially available products *Alcaligenes* sp.-derived lipase include Lipase QLM (trade name, available from Meito Sangyo. Co.).

Examples of the other lipases include Sumizyme CT-L (trade name, available from SHINNIHON CHEMICALS Corporation [*Thermomyces langinosus*-derived lipase]), Lipase AS "Amano" (trade name, available from Amano Enzyme Inc. [*Aspergillus niger*-derived lipase]), Sumizyme NSL3000 (trade name, available from SHINNIHON CHEMICALS Corporation [*Aspergillus niger*-derived lipase]), and Lipase A "Amano"6 (trade name, available from Amano enzyme [*Aspergillus niger*-derived lipase]).

Examples of the protease include Protease M "Amano" (trade name, available from, Amano enzyme [*Aspergillus oryzae*-derived protease]).

Examples of the pectinase include Pectinase G "Amano" (trade name, available from Amano enzyme [*Aspergillus pulverulentus*-derived protease]).

The microorganism-derived enzyme may also be immobilized on a support and used as an immobilized enzyme. Examples of the support used for immobilization of the enzyme include Celite or a Toyonite (Toyonite 200, Toyonite 200P, Toyonite 200M, Toyonite 200A (available from Toyo Denka Kogyo Co., Ltd.)). Other than an immobilized enzyme obtained by immobilizing the above-mentioned commercial lipase, an enzyme immobilized by applying a cultured cell supernatant obtained by culturing a specific microorganism to the above support may be used as an enzyme having lipase activity. As the specific microorganism, *Geotrichum fermentans, Galactomyces aurantii, Galactomyces reessii, Dipodascus australiensis* and the like are preferable.

Subsequently, by oxidizing the hydroxyl group of the compound represented by the formula (III), the compound represented by the formula (IV) is obtained.

In a preferred embodiment of the present reaction, by reacting the compound represented by the formula (III) with an oxidizing agent in the presence of a catalyst, the compound represented by the formula (IV) is obtained.

Examples of the catalyst include $RuCl_3$ and 2,2,6,6-tetramethylpiperidine 1-oxyl (TEMPO).

The amount of catalyst used is not particularly limited as long as it is an amount that does not inhibit the reaction and does not cause a side reaction, but it may usually be used in the range of 0.001 to 1 molar equivalents relative to the compound represented by the formula (III), and preferably in the range of 0.01 to 0.1 molar equivalents.

Examples of the oxidizing agent include sodium hypochlorite.

The amount of oxidizing agent used is not particularly limited as long as it is an amount that does not inhibit the reaction and does not cause a side reaction, but it may usually be used in the range of 1 to 3 molar equivalents relative to the compound represented by the formula (III), and preferably in the range of 1 to 1.5 molar equivalents.

A solvent used in the reaction is not particularly limited as long as it is stable under relevant reaction conditions and does not inhibit the target reaction. Since the yield of the compound represented by the formula (IV), which is a product, depends on the type of solvent, it is preferably dichloromethane, chloroform, chlorobenzene, acetonitrile, and the like, and more preferably dichloromethane.

With regard to the above solvent, one type may be used either singly or combination of two or more types may be used as a mixture.

The amount of reaction solvent used may be 1 to 100 times by mass relative to the compound represented by the formula (III), and is preferably in the range of 3 to 10 times by mass.

The reaction temperature may usually be −20° C. to 50° C., preferably −20° C. to 20° C., and more preferably −10° C. to 0° C.

The reaction time is usually 0.5 hours to 6 hours, and preferably 1 to 3 hours.

Furthermore, the oxidation reaction of the hydroxyl group of the compound represented by the formula (III) may be carried out by a method (for example, Swern oxidation and the like) well known to a person skilled in the art, and the compound represented by the formula (IV) is obtained.

Subsequently, by reacting the compound represented by the formula (IV) with a base or an acid, the compound represented by the formula (V) is obtained.

Examples of the base include an organic amine such as triethylamine or 1,8-diazabicyclo [5.4.0]-7-undecene.

The amount of base used is not particularly limited as long as it is an amount that does not inhibit the reaction and does not cause a side reaction, but it may usually be used in the range of 0.5 to 3 molar equivalents relative to the compound represented by the formula (IV), and preferably in the range of 0.8 to 1.2 molar equivalents.

Examples of the acid include trifluoro methanesulfonic acid and silica gel.

The amount of acid used is not particularly limited as long as it is an amount that does not inhibit the reaction and does not cause a side reaction, but it may usually be used in the range of 0.1 to 3 molar equivalents relative to the compound represented by the formula (IV).

A solvent used in the reaction is not particularly limited as long as it is stable under relevant reaction conditions and does not inhibit the target reaction. It is preferable to use dichloromethane or methanol.

By reacting the compound represented by the formula (V) with the catalyst under hydrogen atmosphere as a reducing agent, the compound represented by the formula (I) is obtained.

Examples of the catalyst include Lindlar catalyst.

The solvent used for the reaction is not specifically limited if it is stable under the relevant reaction condition and does not inhibit the target reaction. Preferably, ethyl acetate is used.

EXAMPLES

More specific examples are illustrated below, but the disclosure of the invention is not limited thereto. Examples 1 to 6 show the process of the Scheme 1. Examples 7 to 10 show the process of the Scheme 2.

Reference Example 1

Mixture of dimethyl fluoro[(1R,5R)-5-hydroxycyclopent-2-en-1-yl]propanedioate (8a) and dimethyl fluoro[(1S,5S)-5-hydroxycyclopent-2-en-1-yl]propanedioate (8b)

[Chemical Formula 14]

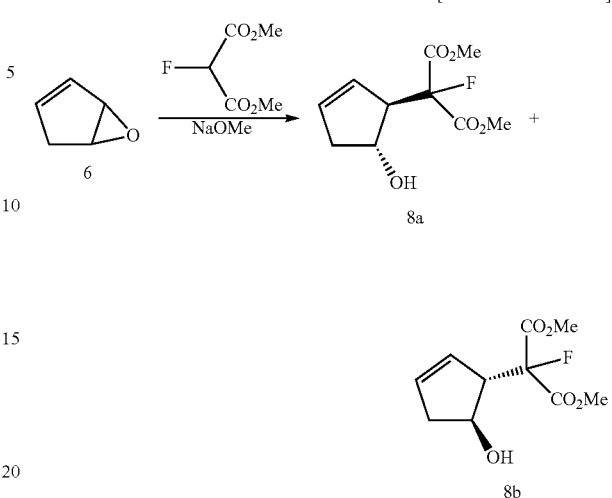

23.81 g (110.2 mmol) of a 25 w/w % methanol solution of sodium methoxide (NaOMe) was added to a methanol (90.4 mL) solution of 18.19 g (121.2 mmol) of dimethyl fluoropropanedioate (7) over 3 minutes while keeping the internal temperature between 25° C. and 38° C. After stirring the solution thus obtained for 15 minutes, 4.52 g (55.1 mmol) of 6-oxabicyclo [3.1.0] hex-2-ene (6) was added thereto over 2 minutes while keeping the internal temperature between 25° C. and 38° C. After stirring at room temperature for 1 hour, 45 mL of a saturated ammonium chloride aqueous solution was added over 10 minutes while keeping the internal temperature between 26° C. and 35° C. The reaction mixture was concentrated under reduced pressure, most of the methanol was removed by evaporation, and 108 g of a brown solution containing solids was obtained. After extraction with 136 mL of ethyl acetate was carried out twice, washing with 45 mL of water was carried out. After the organic layer was concentrated under reduced pressure, 100 mL of toluene was added, and concentration under reduced pressure was carried out again. The concentrated residue was purified by flash silica gel column chromatography (eluent:toluene/ethyl acetate), thus giving 7.21 g of a mixture of the compound of the formula 8a and the compound of the formula 8b as a yellow oily substance.

$^1$H NMR (500 MHz, DMSO-$d_6$): δ(ppm) 2.13-2.17 (m, 1H), 2.56 (dddd, J=2.2, 4.3, 7.1, 17.2 Hz, 1H), 3.32-3.40 (m, 1H), 3.77 (s, 3H), 3.79 (s, 3H), 4.20 (m, 1H), 5.04 (d, J=6.1 Hz, 1H), 5.47 (ddd, J=2.1, 4.3, 6.1 Hz, 1H), 5.85 (ddd, J=2.2, 4.4, 6.1 Hz, 1H). $^{13}$C NMR (125 MHz, DMSO-$d_6$):δ(ppm) 41.93, 53.39 (d, J=19.5 Hz), 58.70 (d, J=20.8 Hz), 70.43 (d, J=2.6 Hz), 93.55, 95.14, 125.59, 133.32, 165.42 (d, J=15.6 Hz), 165.62 (d, J=14.3 Hz). $^{19}$F NMR (470 MHz, DMSO-$d_6$): δ(ppm) −172.43, −172.36. HRMS(ES)m/z: [M+Na]$^+$ calcd for $C_{10}H_{13}O_5FNa$; 255.0645, found 255.0635. IR (neat) 3528, 3408, 2960, 1755, 1438, 1284, 1253, 1173, 1111, 1068, 1031, 936, 838, 787, 722, 668, 415 cm$^{-1}$.

Reference Example 2

Mixture of methyl fluoro[(1R,5R)-5-hydroxycyclopent-2-en-1-yl]acetate (9a) and methyl fluoro[(1S,5S)-5-hydroxycyclopent-2-en-1-yl]acetate (9b)

[Chemical Formula 15]

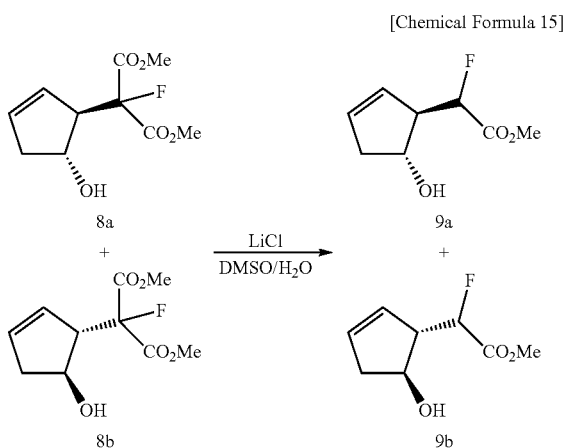 [SMILES: COC(=O)C(F)(C(=O)OC)[C@@H]1C=CC[C@H]1O ; COC(=O)C(F)[C@@H]1C=CC[C@H]1O ; "LiCl" ; COC(=O)C(F)(C(=O)OC)[C@H]1C=CC[C@@H]1O ; COC(=O)C(F)[C@H]1C=CC[C@@H]1O]

172.51 g of dimethyl sulfoxide (DMSO) and 25.92 g of water were added to 17.27 g (74.50 mmol) of a mixture of the compound of the formula 8a and the compound of the formula 8b. 9.65 g (227.65 mmol) of lithium chloride was added to this solution, and the mixture was heated and stirred at 130° C. for 2 hours. After allowing it to cool, the reaction mixture was extracted with 500 mL of ethyl acetate three times, and the organic layer was then concentrated under reduced pressure, thus giving a concentrated residue. This concentrated residue was purified by flash silica gel column chromatography (eluent: n-hexane/ethyl acetate=1:1), thus giving 3.674 g of a mixture of the compound of the formula 9a and the compound of the formula 9b as a yellow oily substance.

$^1$H NMR (500 MHz, DMSO-$d_6$): δ(ppm) 2.11-2.17 (m, 1.6H), 2.53-2.60 (m, 1.6H), 2.87-2.96 (m, 1.6H), 3.71 (s, 1.8H), 3.73 (s, 3H), 4.23-4.28 (m, 1.6H), 4.93 (d, J=5.0 Hz, 0.6H), 5.07 (d, J=5.4 Hz, 1H), 5.11 (dd, J=4.2, 48.3 Hz, 0.6H), 5.17 (dd, J=3.8, 48.5 Hz, 1H), 5.42-5.45 (m, 1H), 5.55-5.58 (m, 0.6H), 5.78-5.80 (m, 1.6H). $^{13}$C NMR (125 MHz, DMSO-$d_6$): δ(ppm) 41.29, 41.83, 51.95, 52.13, 56.80 (d, J=20.8 Hz), 57.06 (d, J=19.5 Hz), 70.49 (d, J=5.2 Hz), 71.90 (d, J=2.6 Hz), 88.36 (d, J=184.3 Hz), 88.48 (d, J=184.3 Hz), 125.93 (d, J=5.2 Hz), 127.28 (d, J=3.9 Hz), 131.76, 132.13, 169.05 (d, J=24.7 Hz), 169.21 (d, J=24.7 Hz). $^{19}$F NMR (470 MHz, DMSO-$d_6$):δ(ppm) −197.87 (dd, J=29.2, 47.5 Hz), −194.53 (dd, J=25.7, 47.8 Hz). HRMS(ES)m/z: [M+Na]$^+$ calcd for $C_8H_{11}O_3FNa$; 197.0590, found 197.0578. IR (neat) 3410, 3060, 2956, 2851, 1747, 1440, 1357, 1288, 1228, 1127, 1097, 1067, 1048, 1025, 952, 856, 724, 584, 450 cm$^{-1}$.

Reference Example 3

Mixture of methyl fluoro[(1R,5R)-5-hydroxycyclopent-2-en-1-yl]acetate (9a) and methyl fluoro[(1S,5S)-5-hydroxycyclopent-2-en-1-yl]acetate (9b)

70.06 g of dimethyl sulfoxide and 45.64 g (33.16 mol) of triethylamine hydrochloride were added to 70.02 g (0.3015 mmol) of a mixture of the compound of the formula 8a and the compound of the formula 8b, and the mixture was heated and stirred at 110° C. to 120° C. for 5 hours. After allowing it to cool, 350.9 g of water was added thereto, and the reaction mixture was extracted with 350 g of methyl isobutyl ketone twice. The organic layer was concentrated under reduced pressure, thus giving 65.40 g of a yellowish brown oily substance containing 46.78 g (value quantitatively determined by gas chromatography) of a mixture of the compound of the formula 9a and the compound of the formula 9b.

Reference Example 4

Mixture of methyl fluoro[(1R,5R)-5-hydroxycyclopent-2-en-1-yl]acetate (9a) and methyl fluoro[(1S,5S)-5-hydroxycyclopent-2-en-1-yl]acetate (9b)

1 mL of dimethyl sulfoxide, 0.073 g (1.25 mmol) of sodium chloride, and 0.061 g (1.00 mmol) of acetic acid were added to 0.232 g (1.00 mmol) of a mixture of the compound of the formula 8a and the compound of the formula 8b, and the mixture was heated and stirred at 110 to 120° C. for 5 hours. After allowing it to cool, analysis was carried out using a high-performance liquid chromatography, and it was found that 0.146 g (the value quantitatively determined by high performance liquid chromatography) of a mixture of the compound of the formula 9a and the compound of the formula 9b was obtained.

Reference Example 5

Mixture of methyl fluoro[(1R,2S,3R,5S)-3-hydroxy-6-oxabicyclo [3.1.0] hex-2-yl]acetate (10a) and methyl fluoro[(1S,2R,3S,5R)-3-hydroxy-6-oxabicyclo [3.1.0] hex-2-yl]acetate (10b)

[Chemical Formula 16]

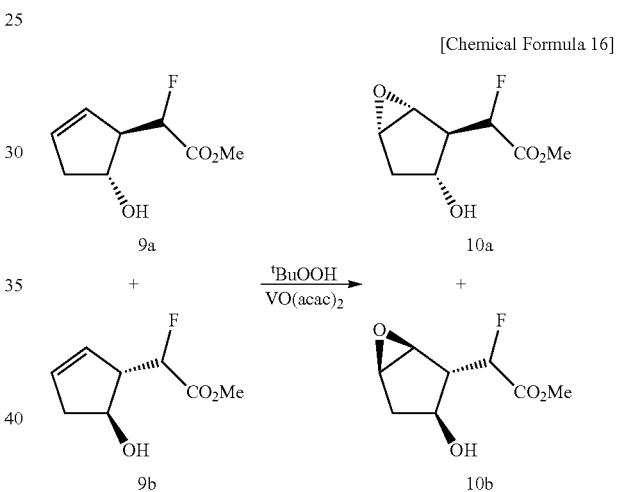

0.1176 g (0.444 mmol) of vanadyl acetylacetonate (VO (acac)$_2$) was added to a chlorobenzene (18.37 g) solution of 3.644 g (20.92 mmol) of a mixture of the compound of the formula 9a and the compound of the formula 9b at room temperature. The mixture was heated to 60° C., and 5.445 g (42.29 mmol) of a 70% toluene solution of tert-butyl hydroperoxide (tBuOOH) was added thereto over 10 minutes while keeping the internal temperature between 55° C. and 60° C. The mixture was stirred at 55° C. for 4 hours and then allowed to cool to room temperature. After 22 g of a 20% sodium thiosulfate aqueous solution was added and stirring was carried out for 30 minutes, extraction was carried out with 50 mL of ethyl acetate four times. The organic layers were combined and concentrated under reduced pressure, thus giving a concentrated residue. This concentrated residue was purified by flash silica gel column chromatography (eluent: n-hexane/ethyl acetate=2:1 to 1:1), thus giving 2.402 g of a mixture of the compound of the formula 10a and the compound of the formula 10b as a yellow oily substance.

$^1$H NMR (500 MHz, DMSO-$d_6$):δ(ppm) 0.1.76 (s, 0.6H), 1.79 (s, 1H), 1.99 (dt, J=7.6, 1.5 Hz, 1H), 2.02 (dt, J=7.6, 1.5 Hz, 0.6H), 2.42-2.44 (m, 0.6H), 2.48-2.51 (m, 1H), 3.38 (d, J=2.5 Hz, 1H), 3.55-3.56 (m, 1.6H), 3.59 (m, 0.6H), 3.75 (s, 1.8H), 3.77 (s, 3H), 4.08 (t, J=6.9 Hz, 0.6H), 4.18 (t, J=6.9 Hz, 1H), 4.41 (d, J=6.5 Hz, 0.6H), 4.49 (d, J=6.1 Hz, 1H), 5.32 (dd, J=4.0, 47.0 Hz, 1H), 5.35 (dd, J=3.0, 48.0 Hz, 0.6H). $^{13}$C NMR (125 MHz, DMSO-$d_6$):δ(ppm) 37.37, 37.88, 51.87 (d, J=19.5 Hz), 51.93 (d, J=18.2 Hz), 52.34, 52.42, 56.83 (d, J=7.8 Hz), 57.73, 57.84, 58.20 (d, J=2.6 Hz), 70.85 (d, J=5.2 Hz), 72.65 (d, J=2.6 Hz), 125.93 (d, J=181.7 Hz), 127.28 (d, J=183.0 Hz), 168.63 (d, J=23.4 Hz), 168.71 (d, J=24.7 Hz). $^{19}$F NMR (470 MHz, DMSO $d_6$):δ(ppm) −198.56 (dd, J=32.9, 47.5 Hz), −198.20 (dd, J=32.9, 48.0 Hz). HRMS (ES)m/z: [M+Na]$^+$ calcd for $C_8H_{11}O_4FNa$; 213.0539, found 213.0530. IR (neat) 3506, 3032, 2959, 1758, 1639, 1440, 1408, 1364, 1288, 1226, 1098, 1077, 1012, 965, 917, 838, 802, 732, 668, 564, 444 cm$^{-1}$.

Reference Example 6

Methyl (1R,2R,4S,5S,6R)-6-fluoro-2,4-dihydroxybicyclo [3.1.0] hexane-6-carboxylate (2)

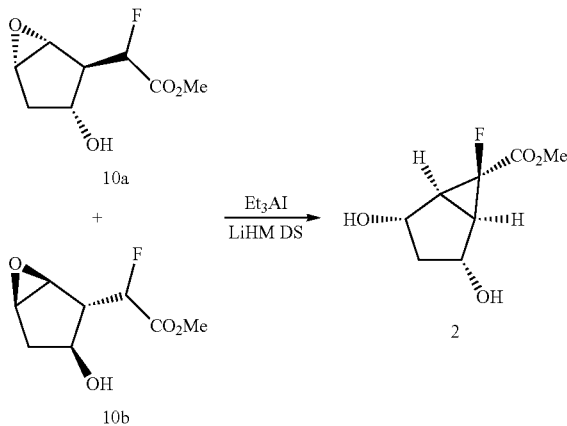

[Chemical Formula 17]

A THF (dehydrated, 20 mL) solution of 2.334 g (12.27 mmol) of a mixture of the compound of the formula 10a and the compound of the formula 10b was cooled to −50° C., and 29.0 mL (27.26 mmol) of a 0.94 mol/L triethyl aluminum (Et$_3$Al) hexane solution was added thereto over 30 minutes while keeping the internal temperature between −60° C. and −50° C. After stirring at −50° C. for 30 minutes, 23.6 mL (23.60 mmol) of a 1 mol/L lithium hexamethyl disilazide (LiHMDS) hexane solution was added thereto over 45 minutes while keeping the internal temperature between −50° C. and −40° C. After stirring at −50° C. for 2 hours, the reaction mixture was added over 30 minutes to 44.3 g of a 25% citric acid aqueous solution cooled to 5° C. This reaction mixture was extracted with 50 mL of ethyl acetate four times and concentrated under reduced pressure. The concentrated residue was purified by flash silica gel column chromatography (eluent:ethyl acetate), thus giving a yellow oily substance. This oily substance was crystallized from a mixed liquid of 3.0 g of ethyl acetate and 0.5 g of water, thus giving 1.027 g of the compound of the formula 2 as colorless crystals.

mp 73.9-76.5° C., $^1$H NMR (500 MHz, DMSO-$d_6$): δ(ppm) 1.64 (dd, J=4.4, 15.3 Hz, 1H), 1.96 (m, 1H), 2.17 (s, 2H), 3.72 (br s, 3H), 4.18 (d, J=5.0 Hz, 2H), 4.93 (br s, 2H). $^{13}$C NMR (125 MHz, DMSO-$d_6$): δ(ppm) 38.03 (d, J=11.7 Hz), 45.76 (d, J=7.8 Hz), 52.64, 71.53, 77.52, 79.42, 168.78 (d, J=26.0 Hz). $^{19}$F NMR (470 MHz, DMSO-$d_6$):δ(ppm) −216.827. HRMS (ES)m/z: [M+Na]$^+$ calcd for $C_8H_{11}O_4FNa$; 213.0539, found 213.0537. IR (KBr) 3549, 3413, 3295, 3246, 2964, 2922, 1732, 1616, 1467, 1442, 1381, 1336, 1285, 1265, 1235, 1198, 1181, 1130, 1078, 1041, 994, 947, 890, 805, 777, 733, 646, 566, 537, 480 cm$^{-1}$.

Example 1

Methyl (1S,2S,4R,5R,6S)-2-(acetyloxy)-6-fluoro-4-hydroxybicyclo [3.1.0] hexane-6-carboxylate (3)

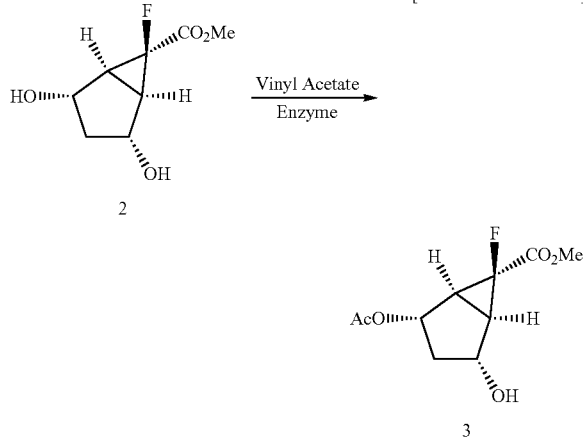

[Chemical Formula 18]

1.6 g of immobilized enzyme Lipase OF/Toyonite 200P which had been prepared in the same manner as the Example 11 (described below) was added to a mixture solution in which 4.0 g of the monohydrate of the compound of the formula 2 is dissolved in 32 mL of tetrahydrofuran (THF) and added with 64 mL of vinyl acetate and 64 mL of toluene, and reacted at room temperature for 18 hours by stirring (600 rpm) using a stirrer. The reaction solution was filtered under reduced pressure using Kiriyama filter paper No. 4 and then the filtrate was concentrated under reduced pressure. The resulting oily substance was subjected to HPLC analysis as described above, and as a result, production of 4.0 g of the compound of the formula 3 (optical purity of 93.2% e.e.) was identified. Part of the oily substance was kept at −20° C. As a result, crystal precipitates were produced and they are washed with a mixture solvent of toluene and n-heptane on a filter paper. As a result of HPLC analysis, the optical purity was 98.1% e.e. The remaining oily substance (including 3.9 g of the compound of the formula 3) was purified by flash silica gel column chromatography using silica gel 60N (purchased from Kanto Chemical Co., Inc.). As a result, 2.84 g (optical purity of 93.14% e.e.) of the compound of the formula 3 was isolated.

$^1$H NMR (500.16 MHz, CDCl$_3$):δ(ppm) 1.96 (m, 1H, J=5.0, 16.4 Hz), 2.11 (s, 3H), 2.28 (ddd, J=6.1,7.3,13.4 Hz, 1H), 2.42 (dd, J=6.5, 14.5 Hz, 1H), 2.44 (dd, J=6.5, 14.5 Hz, 1H), 3.82 (s, 3H), 4.44 (m, 1H), 5.29(m, J=6.1 Hz, 1H). $^{13}$C NMR (125.77 MHz, CDCl$_3$):δ(ppm) 21.22, 35.00 (d, J=10.4 Hz), 37.98 (d, J=11.7 Hz), 42.50 (d, J=9.2 Hz), 52.96, 73.09, 75.56, 168.45, 168.66, 170.23. MS (ESI/APCI Dual positive) m/z 255.0[M+Na]$^-$.

Example 2

Methyl (1S,2S,5R,6R)-2-(acetyloxy)-6-fluoro-4-oxobicyclo [3.1.0] hexane-6-carboxylate (4)

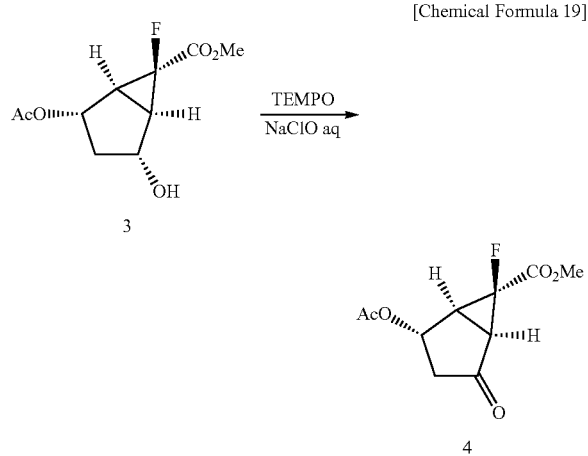

A dichloromethane (dehydrated, 5 mL) solution of 946 mg (4.07 mmol) of the compound of the formula 3 was cooled to −5° C., 14.0 mg (0.090 mmol) of 2,2,6,6-tetramethylpiperidine 1-oxyl (TEMPO), 102.0 mg (1.21 mmol) of sodium hydrogen carbonate, and 2.0 mL of water were added in sequence, and 3.86 g (5.19 mmol) of a 10% sodium hypochlorite aqueous solution was then added while keeping the internal temperature between −5° C. and 0° C. After stirring at −5° C. to 0° C. for 1 hour, the mixture was separated. The organic layer was washed with 1 mL of water and dried over anhydrous sodium sulfate. After concentration under reduced pressure, 899 mg of the compound of the formula 4 was obtained as an oily substance with yellow color.

$^1$H NMR (500.16 MHz, CDCl$_3$):δ(ppm) 2.12 (s, 3H), 2.37 (dd, J=3.4, 19.5 Hz, 1H), 2.65 (dd, J=19.5, 6.1 Hz, 1H), 2.73 (d, J=6.1 Hz, 1H), 2.93 (dd, J=1.9, 6.1 Hz, 1H), 3.83 (s, 3H), 5.50 (d, J=6.1 Hz, 1H). $^{13}$C NMR (125.77 MHz, CDCl$_3$): δ(ppm) 20.88, 38.19 (d, J=11.6 Hz), 39.01 (d, J=13.0 Hz), 43.49 (d, J=3.9 Hz), 53.43, 69.13, 165.78, 165.93, 170.03, 204.35.

Example 3

Methyl (1R, 5R, 6R)-6-fluoro-4-oxo bicyclo [3.1.0] hexa-2-ene-6-carboxylate (5)

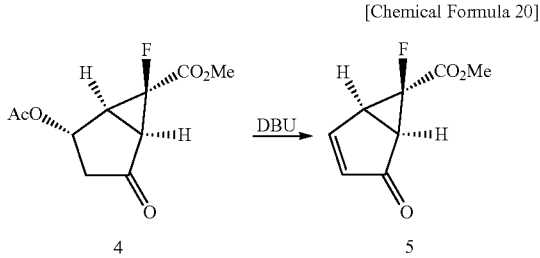

A dichloromethane (18 mL) solution of 719 mg (3.12 mM) of the compound of the formula 4 was added with 0.63 mL (4.07 mmol) of 1,8-diazabicyclo [5.4.0]-7-undecene (DBU), stirred for 1 hour at room temperature, added with 4.2 mL of 1 N hydrochloric acid, and then followed by stirring and liquid fractionation. The aqueous layer was re-extracted with 5 mL of dichlomethane and the organic layer was washed with 5 mL of saturated brine. The organic layer was dried over sodium sulfate and concentrated under reduced pressure. The concentrated residue was purified by flash silica gel column chromatography (eluent:n-hexane/ethyl acetate), thus giving the compound of the formula 5 as a colorless oily substance (413.7 mg).

$^1$H NMR (500.16 MHz, CDCl$_3$):δ(ppm) 2.79 (d, J=5.0Hz, 1H), 3.23 (dd, J=3.0, 6.0 Hz, 1H), 3.86 (s, 3H), 6.06 (d, J=5.5 Hz, 1H), 7.42 (dd, J=3.0, 5.5 Hz, 1H). $^{13}$C NMR (125.77 MHz, CDCl$_3$):δ(ppm) 34.05 (d, J=14.2 Hz), 34.47 (d, J=13.0 Hz), 53.21, 133.34, 152.30 (d, J=2.6 Hz), 165.99, 166.21, 198.56. MS (ESI/APCI Dual positive) m/z 170.9[M+H]$^-$, (ESI/APCI Dual negative) m/z 168.9[M-H]$^-$ Example 4

Methyl (1R, 5R, 6R)-6-fluoro-2-oxo bicyclo [3.1.0] hexane-6-carboxylate (1)

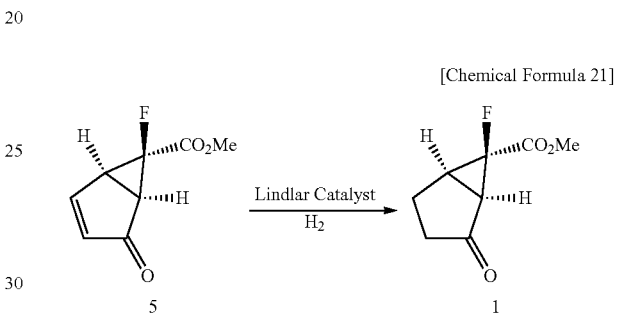

360.7 mg (2.12 mmol) of the compound of the formula 5 was dissolved in 18 mL of ethyl acetate, added with 143 mg of Lindlar catalyst, and stirred for 16 hours under hydrogen atmosphere at room temperature. The obtained solution was filtered through cellulose powder and concentrated under reduced pressure. The concentrated residue was purified by flash silica gel column chromatography (eluent:chloroform), thus giving the compound of the formula 1 as a colorless oily substance (337 mg).

$^1$H NMR (500.16 MHz, CDCl$_3$):δ(ppm) 2.22 (m, 1H), 2.28-2.34 (m, 2H), 2.43 (m, 1H), 2.59 (m, 1H), 2.73 (d, J=2.0 Hz), 3.86 (s, 3H). $^{13}$C NMR (125.77 MHz, CDCl$_3$):δ(ppm) 19.47 (d, J=5.2 Hz), 34.11 (d, J=13.0 Hz), 35.47 (d, J=5.2 Hz), 40.19 (d, J=13.1 Hz), 53.11, 167.46, 167.67, 208.73. MS (ESI/APCI Dual positive) m/z 172.9[M+H]$^-$, TOFMS EI m/z 172.1 [M]$^+$.

Examples 5 to 12 below show the results of examining reaction conditions in order to obtain the compound of the formula 3 by asymmetric acetylation of the compound of the formula 2 using various microorganism-derived enzymes.

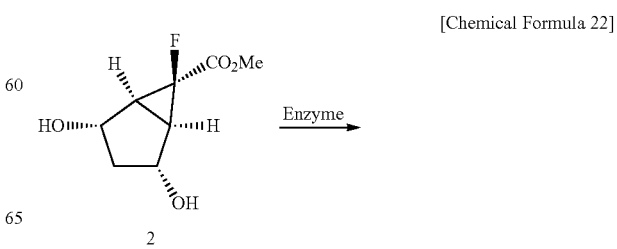

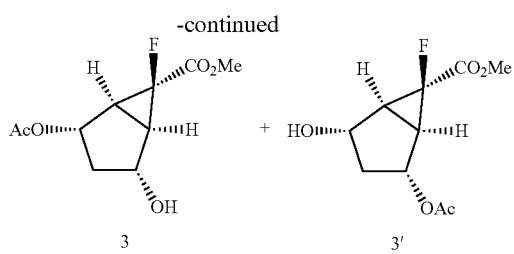

The state of formation of the starting material compound of the formula 2, the target compound of the formula 3 and its enantiomer, the compound of the formula 3', were confirmed by the TLC method and the HPLC method below.

(TLC method: TLC plate; silica gel Si 60 (Art 1.5715, manufactured by Merck & Co., Inc.))

Developing solvent; n-hexane/ethyl acetate=10/1

Coloration; anisaldehyde/conc. sulfuric acid/acetic acid=1/2/100

Rf value; compound of the formula 1=0.20, compounds of the formula 3 and the formula 3'=0.40

(HPLC method: column CHIRALCEL OJ-RH
4.6 mm ID×150 mm L (Daicel Chemical Industries, Ltd.))

Mobile phase; methanol/0.1% phosphoric acid aqueous solution=38/62

Flow rate; 0.8 mL/min

Temperature; 35° C.

Detection; UV 195 nm

Retention time;

compound of the formula 2: 3.8 min compound of the formula 3: 9.0 min compound of the formula 3': 10.3 min Example 5

<Investigation of Enzymes>

50 mg of an enzyme to be tested was placed in a 10 mL stoppered test tube, 2.7 mL of vinyl acetate, 0.3 mL of acetone, and 20 mg of the compound of the formula 2 were added thereto, and stirring was carried out using a stirrer at 25° C. for 18 to 48 hours (600 rpm). After the reaction was completed, enzyme residue was removed by filtration using an Ekicrodisc 25CR (manufactured by Japan Pall Corporation, 25 mm of diameter), the solution was dried under reduced pressure and then dissolved in 1 mL of methanol, and part thereof was then sampled and subjected to TLC analysis and HPLC analysis. The 41 types of enzymes shown in the Table 1, Table 2, and Table 3 were screened.

From the results of TLC analysis, in reactions using the enzymes shown in the Table 1 and Table 2, spots that had an Rf value on TLC coinciding with the Rf value (0.40) of an authentic racemic sample (compound of the formula 3 and compound of the formula 3') and exhibited the same color (brown) were detected. Among enzymes for which the detection of an acetylated form was prominent in the TLC analysis, those for which the target product compound of the formula 3 was confirmed by HPLC analysis are shown in the Table 1 with the amount of target product formed and the optical purity. Furthermore, among enzymes for which the detection of an acetylated form was prominent in the TLC analysis, those for which the optical isomer compound of the formula 3', which is different from the target product, was confirmed by HPLC analysis are shown in the Table 2 with the amount thereof formed and the optical purity.

In the present Examples, enzymes for which formation of neither the compound of the formula 3 nor the compound of the formula 3' was detected are shown in the Table 3.

TABLE 1

| ENZYME NAME | DERIVED FROM | AMOUNT OF 3 FORMED (mg) | % E.E. OF 3 |
| --- | --- | --- | --- |
| Lipase from *Candida cylindracea* | *Candida cylindracea* | 13.57 | 66.04 |
| Lipase AYS "Amano" | *Candida rugosa* | 4.54 | 36.99 |
| Lipase AK "Amano" 20 | *Pseudomonas fluorescens* | 3.15 | 34.41 |
| Lipase AY "Amano" 30G | *Candida rugosa* | 1.84 | 48.06 |
| Sumizyme CT-L | *Thermomyces langinosus* | 1.64 | 99.99 |
| Lipase R "Amano" | *Penicillium roqueforti* | 0.67 | 99.99 |
| Lipase AS "Amano" | *Aspergillus niger* | 0.57 | 57.18 |
| Lipase A "Amano" 6 | *Aspergillus niger* | 0.52 | 49 |
| Lipase PS "Amano" SD | *Burkholderia cepacia* | 0.51 | 25.5 |
| CHE "Amano" 2 | *Pseudomonas* sp. | 0.43 | 48.02 |
| Sumizyme NSL3000 | *Aspergillus niger* | 0.39 | 99.99 |
| Pectinase G "Amano" | *Aspergillus pulverulentus* | 0.32 | 99.99 |
| Nuclease "Amano" G | *Penicillium citrinum* | 0.13 | 99.99 |

TABLE 2

| ENZYME NAME | DERIVED FROM | AMOUNT OF 3' FORMED (mg) | % E.E. OF 3' |
| --- | --- | --- | --- |
| Lipase A CLEA | *Candida antarctica* | 17.82 | 94.06 |
| Novozym 735 | *Candida antarctica* | 14.25 | 96.34 |
| Lipozym TL 100L IM | *Thermomyces langinosus* | 2.93 | 39.87 |
| Novozym 435 | *Candida antarctica* | 0.17 | 99.99 |

TABLE 3

| ENZYME NAME (TRADE NAME) | DERIVED FROM |
| --- | --- |
| Acylase 15000 | *Aspergillus melleus* |
| Protease P "Amano" | *Aspergillus melleus* |
| Lipase M "Amano" 10 | *Mucor javanicus* |
| Deamizyme | *Aspergillus melleus* |
| Lipase II | Porcine Pancreas |
| Lipozyme IM20 | *Rhizomucor miehei* |
| Lactase F | *Aspergillus oryzae* |
| Lipase F-AP-15 | *Rhizopus oryzae* |
| Papain W-40 | *Carica papaya* |
| Lipase G | *Penicillium camemberti* |
| Protease M "Amano" | *Aspergillus oryzae* |
| Protease N "Amano" G | *Bacillus subtilis* |
| Newlase F3G | *Rhizopus niveus* |
| Protease S "Amano" G | *Bacillus stearothermophilus* |
| Sumizyme PLE | *Aspergillus niger* |
| Catalase Nagase | *Micrococcus lysodeikticus* |

TABLE 3-continued

| ENZYME NAME (TRADE NAME) | DERIVED FROM |
|---|---|
| Amylase AD "Amano" | Bacillus subtilis |
| Sumizyme PGO | Penicillium chrysogenum |
| Novozym CALBL | Candida antarctica |
| Bromelain F | Ananas comosus M |
| Proleather FG | Bacillus sp. |
| Sumityme MMR | Rhizomucor miehei |
| Lipozym TL 100 | Thermomyces langinosus |
| Subtilicin A | Bacillus subtilis |

Example 6

<Preparation of Immobilized Enzymes>

0.5 g of each of the eleven kinds of enzyme (trade names: Sumizyme NSL3000 and Sumizyme CT-L manufactured by SHINNIHON CHEMICALS Corporation, trade names: Nuclease "Amano" G, Pectinase G "Amano", Lipase A "Amano" 6, Lipase AY "Amano" 30G, Lipase PS "Amano" SD, Lipase AK "Amano" 20, Lipase AYS "Amano" and Lipase R manufactured by Amano Enzyme, trade name: Lipase Candida cylindracea manufactured by Sigma-Aldrich Japan Co.) (only liquid enzyme Sumizyme CT-L that was used in an amount of 2.0 mL) was dissolved in 10 mL of 100 mM potassium phosphate buffer solution (pH 7) at room temperature (insoluble matters were filtered using Kiriyama filter paper No. 5B) and mixed with 0.5 g of Toyonite 200M (purchased from TOYO DENKA KOGYO CO., LTD.) as an immobilization support within the 15 mL SUMILON tube (manufactured by Sumitomo Bakelite Co., Ltd.), and shaken at 160 rpm for 18 hours at 20° C. After the shaking, each mixture was filtered through Kiriyama filter paper No. 704 (manufactured by Nihon Rikagaku Industry Co., Ltd.) and dried overnight under reduced pressure at room temperature, thus giving each types of immobilized enzymes.

By following the same process, the same eleven kinds of the enzymes were mixed with 0.5 g of Toyonite 200P (purchased from TOYO DENKA KOGYO CO., Ltd.) as an immobilization support, thus giving each type of immobilized enzymes.

Example 7

<Test for Measuring Compound Conversion Capability of Immobilized Enzymes>

50 mg of each of the twenty two types of immobilized enzymes obtained from the Example 6 and 25 mg of the compound of the formula 2 were mixed to 1 mL of vinyl acetate solution containing 10% acetone (volume), and the enzyme reaction was carried out by stirring for 18 hours using an inverting stirrer (600 rpm, inverted with an interval of 2.5 min) at room temperature. After the enzyme reaction was completed, the reaction solution was filtered using an Ekicrodisc 25CR (manufactured by Japan Pall Corporation), and the solution was dried under reduced pressure, dissolved in 1 mL of methanol, and then subjected to HPLC analysis. The results obtained from the HPLC analysis are shown in the Table 4.

TABLE 4

| ENZYME NAME/SUPPORT FOR IMMOBILIZATION | ORIGIN OF ENZYME | AMOUNT OF 3 FORMED (mg) | % E.E. OF 3 |
|---|---|---|---|
| Sumizyme NSL3000/Toyonite200M | Aspergillus niger | 1.69 | 0 |
| Sumizyme CT-L/Toyonite200M | Thermomyces langinosus | NOT DETECTED | |
| Nuclease "Amano" G/Toyonite200M | Penicillium citrinum | NOT DETECTED | |
| Pectinase G "Amano"/Toyonite200M | Aspergillus pulverulentus | 11.18 | 77.6 |
| Lipase A "Amano" 6/Toyonite200M | Aspergillus niger | 0.64 | 28.3 |
| Lipase AY "Amano" 30G/Toyonite200M | Candida rugosa | 17.8 | 75.9 |
| Lipase PS "Amano" SD/Toyonite200M | Burkholderia cepacia | 7.3 | 12.5 |
| Lipase AK "Amano" 20/Toyonite200M | Pseudomonas fluorescens | 13.35 | 39.4 |
| Lipase AYS "Amano"/Toyonite200M | Candida rugosa | 8.38 | 76 |
| Lipase R/Toyonite200M | Penicillium roqueforti | 1.03 | >99 |
| Lipase from Candida cylindracea/Toyonite200M | Candida cylindracea | 12.68 | 80.3 |
| Sumizyme NSL3000/Toyonite200P | Aspergillus niger | 1.75 | 57.2 |
| Sumizyme CT-L/Toyonite200P | Thermomyces langinosus | NOT DETECTED | |
| Nuclease "Amano" G/Toyonite200P | Penicillium citrinum | NOT DETECTED | |
| Pectinase G "Amano"/Toyonite200P | Aspergillus pulverulentus | 1.38 | 77.5 |
| Lipase A "Amano" 6/Toyonite200P | Aspergillus niger | 1.4 | 72.3 |
| Lipase AY "Amano" 30G/Toyonite200P | Candida rugosa | 21.92 | 81.6 |
| Lipase PS "Amano" SD/Toyonite200P | Burkholderia cepacia | 6.29 | 28 |
| Lipase AK "Amano" 20/Toyonite200P | Pseudomonas fluorescens | 8.38 | 43.7 |
| Lipase AYS "Amano"/Toyonite200P | Candida rugosa | 18.17 | 67.1 |
| Lipase R "Amano"/Toyonite200P | Penicillium roqueforti | 3.59 | 83.8 |
| Lipase from Candida cylindracea/Toyonite200P | Candida cylindracea | 9.93 | 72.6 |

Example 8

<Preparation of Immobilized Enzyme and Test for Measuring Compound Conversion Capability>

Each of the fifteen types of enzymes (see, the Table 5) was dissolved in 10 mL of 100 mM of potassium phosphate buffer solution (pH 7) at room temperature, in which the solid enzyme is used in an amount of 0.5 g and the liquid enzyme is used in an amount of 2.0 mL (insoluble matters were filtered through Kiriyama filter paper No. 5B). After that, each mixture was mixed with 0.5 g of Toyonite 200M (purchased from TOYO DENKA KOGYO CO., LTD.) which is an immobilization support within a 15 mL volume SUMILON tube (manufactured by Sumitomo Bakelite Co., Ltd.), and then shaken at 150 rpm for 17 hours at 25° C. After the shaking, each mixture was filtered through Kiriyama filter paper No. 704 (manufactured by Nihon Rikagaku Industry Co., Ltd.) and dried overnight under reduced pressure at room temperature, thus giving each types of immobilized enzymes.

50 mg of each of the fifteen types of the immobilized enzyme and 25 mg of the compound of the formula 2 were mixed to 1 mL of vinyl acetate solution containing 10% acetone (volume), and the enzyme reaction was carried out by stirring for 18 hours using an inverting stirrer (600 rpm, inverted with an interval of 2.5 min) at room temperature. After the enzyme reaction was completed, the reaction solution was filtered using an Ekicrodisc 25CR (manufactured by Japan Pall Corporation), and the solution was dried under reduced pressure, dissolved in 1 mL of methanol, and then subjected to HPLC analysis. The results obtained from the HPLC analysis are shown in the Table 5.

20 to 40 mg of each of the 111 types of the immobilized enzyme that are obtained by the above was placed in a sample tube having screw stopper with 3.5 mL volume, and added with a solution in which 40 mg of the crystals of the compound of the formula 2 is added with 1.8 mL of vinyl acetate and 0.2 mL of acetone, and the reaction was carried out by stirring for 18 to 21 hours at room temperature using a stirrer (600 rpm). After the reaction was completed, the immobilized

TABLE 5

| ENZYME NAME/SUPPORT FOR IMMOBILIZATION | ORIGIN OF ENZYME | AMOUNT OF 3 FORMED (mg) | % E.E. OF 3 |
|---|---|---|---|
| Acylase 15000/Toyonite200M | Aspergillus melleus | 0 | |
| Protease P "Amano"/Toyonite200M | Aspergillus melleus | 0.27 | 17.4 |
| Lipase M "Amano10"/Toyonite200M | Mucor javanicus | 0 | |
| Sumizyme PLE/Toyonite200M | Aspergillus niger | 0 | |
| Deamizyme/Toyonite200M | Aspergillus melleus | 0 | |
| Lipase II/Toyonite200M | Porcine pancreas | 0 | |
| Lipase F/Toyonite200M | Aspergillus oryzae | 0 | |
| Lipase F-AP-15/Toyonite200M | Rhizopus oryzae | 0.83 | 18.5 |
| Novozym CALB/Toyonite200M | Candida antarctica | 0 | |
| Bromelain F/Toyonite200M | Ananas comosus M | 0 | |
| Protease "Amano" G/Toyonite200M | Bacillus subtilis | 0 | |
| Newlase F3G/Toyonite200M | Rhizopus niveus | 0 | |
| Protease S "Amano" G/Toyonite200M | Bacillus stearothermophilus | 0 | |
| Protease M "Amano"/Toyonite200M | Aspergillus oryzae | 0.34 | 72.9 |
| Proleather FG/Toyonite200M | Bacillus sp. | 0.41 | 26.5 |
| Sumizyme MMR/Toyonite200M | Rhizomucor miehei | 0 | |
| Lipozym TL 100/Toyonite200M | Candida rugosa | 0 | |
| Subtilicin A/Toyonite200M | Bacillus subtilis | 0 | |

Example 9

<Preparation of Immobilized Enzyme and Test for Measuring Compound Conversion Capability>

111 strains of filamentous fungus were subjected to aeration agitation culture in a 200 mL Erlenmeyer flask containing 40 mL of a medium formed from defatted rice bran 3%, corn steap liquor 3%, soybean oil 1%, and ammonium sulfate 0.2% (pH 6) at 18° C. to 28° C. for 3 days. After culturing was completed, each microorganism culture fluid was individually transferred to a centrifuge tube, and the culture fluid was centrifuged into cells and cell supernatant by a centrifuge (8000 rpm, 12 to 15 minutes). 0.1 volume of a 1 M potassium phosphate pH 7 buffer and 0.5 g of Toyonite 200M (purchased from TOYO DENKA KOGYO CO., LTD) as a support were added to each microorganism cell supernatant thus obtained (in a centrifuge tube such as a Sumilon tube) and shaken at 25° C. overnight (maximum 20 hours). After shaking was completed, the mixture was allowed to stand for 5 minutes; after the insoluble matters including the support settled down on the bottom of the centrifuge tube, an upper layer solution was removed by decantation, 15 mL of a 0.1 M potassium phosphate pH 7 to pH 7.5 buffer was added, and resuspension by stirring was carried out. This was repeated a total of two times, and the suspension was filtered under reduced pressure using a Kiriyama funnel (trade name) equipped with Kiriyama filter paper No. 5B (trade name), thus giving each of the microorganism culture fluid supernatant-derived immobilized enzymes on the filter papers. Each immobilized enzyme was filtered and dried under reduced pressure for a few minutes on the filter, placed in a vacuum desiccator (with dry silica gel), and dried overnight (maximum 20 hours). Each of the immobilized enzymes that had completed drying was used in the enzymatic reaction below.

enzyme was removed by filtration using an Ekicrodisc 25CR, and the solution was dried under reduced pressure, dissolved in 1 mL of methanol, and then subjected to the HPLC analysis.

For a case in which a significant amount of the compound of the compound with the formula 3 is produced as a target product, the amount of the target product formed and its optical purity are shown in the Table 6.

TABLE 6

| MICROORGANISM AS ORIGIN OF ENZYME (SUPPORT FOR IMMOBILIZATION IS TOYONITE 200M FOR ALL CASES) | AMOUNT OF 3 FORMED (mg) | % E.E. OF 3 |
|---|---|---|
| Geotrichum fermentans JCM2467 | 5.48 | 72.8 |
| Dipodascus australiensis NBRC10805 | 3.04 | 63.1 |
| Galactomyces citri-aurantii NBRC10821 | 2.16 | 55.7 |
| Galactomyces reessii JCM1942 | 3.73 | 53.3 |
| Geotrichum capitatum JCM3908 | 2.52 | 48.7 |
| Dipodascus armillariae NBRC10803 | 3.35 | 43.6 |
| Dipodascus armillariae NBRC10802 | 1.48 | 40.8 |

Example 10

<Preparation of Immobilized Enzyme and Test for Measuring Compound Conversion Capability>

4 g of each of Lipase TL, Lipase PL, Lipase OF and Lipase QLM (all obtained from Meito Sangyo. Co.) was dissolved in 150 mL of 100 mM potassium phosphate buffer solution (pH 7) at room temperature, and added with 1 g of the support, Toyonite 200M (purchased from TOYO DENKA KOGYO CO., LTD.), and shaken at 150 rpm for 19 hours at room temperature by using a shaker. After shaking was completed, the mixture was allowed to stand for 5 minutes; after the insoluble matters containing the support settled down on the bottom of the centrifuge tube, an upper layer solution was removed by decantation, 15 mL of a 0.1 M potassium phosphate pH 7 to pH 7.5 buffer was added, and resuspension by stirring was carried out. This was repeated a total of two times, and the suspension was filtered under reduced pressure using a Kiriyama funnel (trade name) equipped with Kiriyama filter paper No. 5B (trade name), thus obtaining each immobilized enzyme on the filter paper. 50 mg of each of the four types of the immobilized enzyme that are obtained by the above was placed in a sample tube having screw stopper with 3.5 mL volume, and added with a solution in which 40 mg of the crystals of the compound of the formula 2 is added with 1.8 mL of vinyl acetate and 0.2 mL of acetone, and the reaction was carried out by stirring for 16 hours at room temperature using a stirrer (600 rpm). After the reaction was completed, the immobilized enzyme was removed by filtration using an Ekicrodisc 25CR, and the solution was dried under reduced pressure, dissolved in 1 mL of methanol, and then subjected to the HPLC analysis. The results obtained from the HPLC analysis are shown in the Table 7.

completed, the mixture solution including the support and the enzyme was filtered under reduced pressure through Kiriyama filter paper No. 4, suspended and washed with 40 mL of 100 mM potassium phosphate buffer solution (pH 7), and filtered and dried under reduced pressure to obtain each immobilized enzyme. 40 mg of each of the immobilized enzymes that are obtained from the above and Lipase TL, Lipase PL, Lipase OF and Lipase QLM was placed in a sample tube having screw stopper with 3.5 mL volume, and added with a solution in which 80 mg of the crystals of the compound of the formula 2 is added with 1.8 mL of vinyl acetate and 0.2 mL of acetone, and the reaction was carried out by stirring for 18 hours at 25° C. using a stirrer (600 rpm).

TABLE 7

| ENZYME NAME/ SUPPORT FOR IMMOBILIZATION | ORIGIN OF ENZYME | AMOUNT OF 3 FORMED (mg) | % E.E. OF 3 |
| --- | --- | --- | --- |
| Lipase PL/Toyonite200M | Alcaligenes sp. | NOT DETECTED | |
| Lipase OF/Toyonite200M | Candida cylindracea | 34.87 | 86.5 |
| Lipase QLM/Toyonite200M | Alcaligenes sp. | 31.14 | 80.5 |
| Lipase TL/Toyonite200M | Pseudomonas stutzeri | 22.10 | 32.9 |

Example 11

<Preparation of Immobilized Enzyme and Test for Measuring Compound Conversion Capability>

2 g of each of Lipase OF and Lipase QLM was placed in two separate plastic bottles, dissolved in 100 mM of potassium phosphate buffer solution (pH 7) (that is, four solutions are prepared in total), and mixed with 4 g of Toyonite 200M or Toyonite 200P, thus yielding four combinations of enzyme and support. The resultant was shaken at 120 rpm for 18 hours at room temperature by using a shaker. After shaking was completed, The immobilized enzyme (four types) was separately subjected to the reaction with the same condition and reaction temperature of 16° C. After the reaction was completed, the immobilized enzyme was removed by filtration using an Ekicrodisc 25CR, and the solution was dried under reduced pressure, dissolved in 1 mL of methanol, and then subjected to the HPLC analysis. The results obtained from the HPLC analysis are shown in the Table 8.

TABLE 8

| ENZYME NAME/SUPPORT FOR IMMOBILIZATION REACTION TEMPERATURE | ORIGIN OF ENZYME | AMOUNT OF 3 FORMED (mg) | % E.E. OF 3 |
| --- | --- | --- | --- |
| Lipase PL 25° C. | Alcaligenes sp. | NOT DETECTED | |
| Lipase OF 25° C. | Candida cylindracea | 1.06 | 51.9 |
| Lipase QLM 25° C. | Alcaligenes sp. | 63.45 | 78.2 |
| Lipase TL 25° C. | Pseudomonas stutzeri | NOT DETECTED | |
| Lipase OF/Toyonite200M 25° C. | Candida cylindracea | 80.32 | 87.3 |
| Lipase OF/Toyonite200P 25° C. | Candida cylindracea | 81.35 | 87.0 |
| Lipase QLM/Toyonite200M 25° C. | Alcaligenes sp. | 68.23 | 75.0 |
| Lipase QLM/Toyonite200P 25° C. | Alcaligenes sp. | 57.87 | 77.6 |
| Lipase OF/Toyonite200M 16° C. | Candida cylindracea | 70.80 | 89.3 |
| Lipase OF/Toyonite200P 16° C. | Candida cylindracea | 74.22 | 87.1 |
| Lipase QLM/Toyonite200M 16° C. | Alcaligenes sp. | 35.97 | 80.0 |
| Lipase QLM/Toyonite200P 16° C. | Alcaligenes sp. | 33.74 | 77.3 |

Example 12

<Test with Modified Enzyme Amount and Composition of Reaction Solution>

1.0 g of the monohydrate compound of the formula 2 was dissolved in 8 mL of THF, and added with 103 mg of Lipase OF/Toyonite 200P, that is, immobilized enzyme produced in the same manner as the Example 7, in a mixture solution of 16 mL of vinyl acetate and 16 mL of toluene, and subjected to the reaction for 24 hours at room temperature by stirring (600 rpm) using a stirrer. The reaction solution was filtered under reduced pressure through the Kiriyama filter paper No. 5B. The filtrate was concentrated under reduced pressure and the resulting oily substance was analyzed by HPLC by following the method described above. As a result, it was found that the compound of the formula 3 is produced in an amount of 1.0 g (optical purity of 91.7% e.e.).

Industrial Applicability

According to the invention, 2-amino-3-alkoxy-6-fluoro bicyclo [3.1.0] hexane-2,6-dicarboxylic acid derivative, which is an antagonist of mGluR2/mGluR3, and a pharmaceutically acceptable salt thereof can be synthesized in a large amount with low cost by using inexpensive reacting materials.

The invention claimed is:

1. A process for producing a compound represented by the formula (I) or a salt thereof comprising:

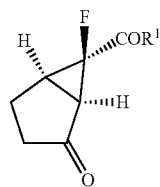

(I)

(in the formula (I), $R^1$ represents
(1) —OH,
(2) —O—$R^a$, or
(3) —$NR^bR^c$,
$R^a$ represents a $C_{1-6}$ alkyl group or a $C_{3-8}$ cycloalkyl group (wherein the $C_{1-6}$ alkyl group or $C_{3-8}$ cycloalkyl group is either unsubstituted or substituted with one or more of a $C_{1-6}$ alkoxy group, a hydroxyl group, a halogen atom, an aryl group, or a heteroaryl group),
$R^b$ and $R^c$, which may be the same or different from each other, each represents a hydrogen atom, a halogen atom, a $C_{1-6}$ alkyl group, or a $C_{3-8}$ cycloalkyl group (the $C_{1-6}$ alkyl group or $C_{3-8}$ cycloalkyl group is either unsubstituted or substituted with one or more of a hydroxyl group, a $C_{1-6}$ alkoxy group, an aryl group, or a heteroaryl group), or $R^b$ and $R^c$ may bond to each other and form a 4- to 7-membered saturated heterocycle together with an adjacent nitrogen atom (wherein the saturated heterocycle is either unsubstituted or substituted with a hydroxyl group, a $C_{1-6}$ alkyl group, or a $C_{1-6}$ alkoxy group))

(A) converting a compound represented by the formula (II) to a compound represented by the formula (III), wherein the compound represented by Formula (III) is produced by reacting the compound represented by Formula (II) with an acyl group donor in the presence of an enzyme derived from a microorganism or Fungus,

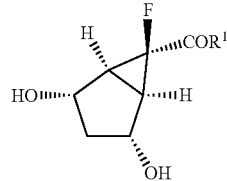

(II)

(in the formula (II), $R^1$ is as defined in the formula (I) above)

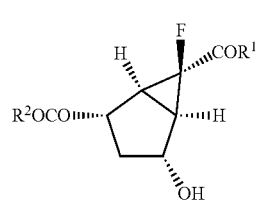

(III)

(in the formula (III), $R^1$ is as defined in the formula (I) above,
$R^2$ represents a hydrogen atom, a $C_{1-6}$ alkyl group, a $C_{3-8}$ cycloalkyl group, or a —$(CH_2)_n$-phenyl group (wherein the $C_{1-6}$ alkyl group, $C_{3-8}$ cycloalkyl group, or —$(CH_2)_n$-phenyl group is either unsubstituted or substituted with one or more of a halogen atom, a hydroxyl group, a $C_{1-6}$ alkyl group, or a $C_{1-6}$ alkoxy group), and n represents 0, 1, or 2)

(B) converting the compound represented by the formula (III) to a compound represented by the formula (IV),

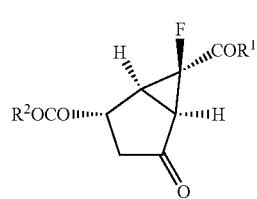

(IV)

(in the formula (IV), $R^1$ and $R^2$ are as defined in the formula (I) and the formula (III) above), (C) converting the compound represented by the formula (IV) to a compound represented by the formula (V),

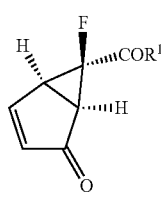

(V)

(in the formula (V), $R^1$ is as defined in the formula (I) above), and (D) converting the compound represented by the formula (V) to the compound represented by the formula (I).

2. A process for producing a compound represented by the formula (III) or a salt thereof, which comprises converting a compound represented by the formula (II) to a compound represented by the formula (III), wherein the compound represented by Formula (III) is produced by reacting the compound represented by Formula (II) with an acyl group donor in the presence of an enzyme derived from a microorganism or fungus,

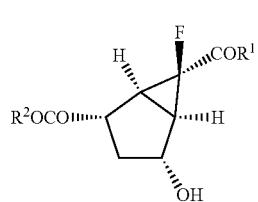

(III)

(in the formula (III), $R^1$ represents
(1) —OH,
(2) —O—$R^a$, or
(3) —$NR^b R^c$,
$R^a$ represents a $C_{1-6}$ alkyl group or a $C_{3-8}$ cycloalkyl group (wherein the $C_{1-6}$ alkyl group or $C_{3-8}$ cycloalkyl group is either unsubstituted or substituted with one or more of a $C_{1-6}$ alkoxy group, a hydroxyl group, a halogen atom, an aryl group, or a heteroaryl group),
$R^b$ and $R^c$, which may be the same or different from each other, each represents a hydrogen atom, a halogen atom, a $C_{1-6}$ alkyl group, or a $C_{3-8}$ cycloalkyl group (wherein the $C_{1-6}$ alkyl group or $C_{3-8}$ cycloalkyl group is either unsubstituted or substituted with one or more of a hydroxyl group, a $C_{1-6}$ alkoxy group, an aryl group, or a heteroaryl group), or $R^b$ and $R^c$ bond to each other and form a 4- to 7-membered saturated heterocycle together with an adjacent nitrogen atom (wherein the saturated heterocycle is either unsubstituted or substituted with a hydroxyl group, a $C_{1-6}$ alkyl group, or a $C_{1-6}$ alkoxy group),
$R^2$ represents a hydrogen atom, a $C_{1-6}$ alkyl group, a $C_{3-8}$ cycloalkyl group, or a —$(CH_2)_n$-phenyl group (wherein the $C_{1-6}$ alkyl group, $C_{3-8}$ cycloalkyl group, or —$(CH_2)_n$-phenyl group is either unsubstituted or substituted with one or more of a halogen atom, a hydroxyl group, a $C_{1-6}$ alkyl group, or a $C_{1-6}$ alkoxy group), and n represents 0, 1, or 2)

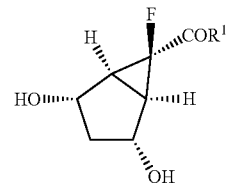

(II)

(in the formula (II), $R^1$ is as defined in the formula (III) above).

3. The process according to claim 1 or 2, wherein $R^1$ is (2)—O—$R^a$ and $R^a$ is a methyl group or an ethyl group.

4. The process according to claim 1 or 2, wherein $R^2$ is a methyl group.

5. The process according to claim 1 or 2, wherein the microorganism is at least one selected from the group consisting of the genus *Candida*, the genus *Aspergillus*, the genus *Thermomyces*, the genus *Penicillium*, the genus *Alcaligenes*, the genus *Geotrichum*, the genus *Galactomyces*, and the genus *Dipodascus*.

6. The process according to claim 1 or 2, wherein the enzyme derived from the microorganism is a lipase, a protease, or a pectinase.

7. The process according to claim 1 or 2, wherein the enzyme derived from the microorganism is a lipase derived from *Candida cylindracea*, *Candida rugosa*, or *Alcaligenes sp*.

8. The process according to claim 1 or 2, wherein the enzyme is immobilized on a support.

9. The process according to claim 1 or 2, wherein the acyl group donor is vinyl acetate or isopropenyl acetate.

\* \* \* \* \*